US011633595B2

(12) United States Patent
Weisend

(10) Patent No.: US 11,633,595 B2
(45) Date of Patent: Apr. 25, 2023

(54) SYSTEM FOR VARIABLY CONFIGURABLE, ADAPTABLE ELECTRODE ARRAYS AND EFFECTUATING SOFTWARE

(71) Applicant: StimScience Inc., Berkeley, CA (US)

(72) Inventor: Michael P. Weisend, Yellow Springs, OH (US)

(73) Assignee: STIMSCIENCE INC., Berkeley, CA (US)

( * ) Notice: Subject to any disclaimer, the term of this patent is extended or adjusted under 35 U.S.C. 154(b) by 124 days.

(21) Appl. No.: 17/170,521

(22) Filed: Feb. 8, 2021

(65) Prior Publication Data

US 2021/0228877 A1 Jul. 29, 2021

Related U.S. Application Data

(63) Continuation of application No. 15/290,391, filed on Oct. 11, 2016, now Pat. No. 10,946,196, which is a
(Continued)

(51) Int. Cl.
*A61N 1/36* (2006.01)
*A61B 5/055* (2006.01)
(Continued)

(52) U.S. Cl.
CPC ........ *A61N 1/36025* (2013.01); *A61B 5/0075* (2013.01); *A61B 5/055* (2013.01);
(Continued)

(58) Field of Classification Search
CPC .............. A61N 1/36025; A61N 1/0456; A61N 1/0476; A61N 1/3603; A61N 1/0526;
(Continued)

(56) References Cited

U.S. PATENT DOCUMENTS 7,885,706 B2  2/2011  Ludvig et al.
8,583,238 B1  11/2013  Heldman et al.
(Continued)

FOREIGN PATENT DOCUMENTS

EP      2314346 A1   4/2011
WO  2016110804 A1   7/2016
(Continued)

OTHER PUBLICATIONS

U.S. Appl. No. 16/195,634, Final Rejection, dated Sep. 2, 2020, 16 pgs.
(Continued)

*Primary Examiner* — Tammie K Marlen
(74) *Attorney, Agent, or Firm* — Schwegman Lundberg & Woessner, P.A.

(57) ABSTRACT

Electrical non-invasive brain stimulation (NIBS) delivers weak electrical currents to the brain via electrodes that are affixed to the scalp. NIBS can excite or inhibit the brain in areas that are impacted by that electrical current during and for a short time following stimulation. Electrical NIBS can be used to change brain structure in terms of increasing white matter integrity as measured by diffusion tensor imaging. Together the electrical NIBS can induce changes in brain structure and function. The present methods and devices are adaptable to and configurable for facilitating the enhancement of brain performance, and the treatment of neurological diseases and tissues. The present methods and devices are advantageously designed to utilize modern electrodes deployed with, inter alia, various spatial arrangements, polarities, and current strengths to target brain areas or networks to thereby enhance performance or deliver therapeutic interventions.

29 Claims, 17 Drawing Sheets

Related U.S. Application Data continuation-in-part of application No. 14/083,379, filed on Nov. 18, 2013, now abandoned.

(60) Provisional application No. 61/962,698, filed on Nov. 14, 2013, provisional application No. 61/796,634, filed on Nov. 16, 2012.

(51) Int. Cl.

| *A61B 6/03* | (2006.01) |
|---|---|
| *A61B 5/00* | (2006.01) |
| *A61N 1/04* | (2006.01) |
| *A61B 5/245* | (2021.01) |
| *A61B 5/291* | (2021.01) |
| *A61B 5/369* | (2021.01) |
| *A61N 2/00* | (2006.01) |
| *A61N 7/00* | (2006.01) |
| *A61N 1/05* | (2006.01) |

(52) U.S. Cl.
CPC .............. *A61B 5/245* (2021.01); *A61B 5/291* (2021.01); *A61B 5/369* (2021.01); *A61B 5/4064* (2013.01); *A61B 5/4836* (2013.01); *A61B 6/037* (2013.01); *A61N 1/0456* (2013.01); *A61N 1/0476* (2013.01); *A61B 5/4094* (2013.01); *A61B 5/4812* (2013.01); *A61N 1/0526* (2013.01); *A61N 1/3603* (2017.08); *A61N 2/006* (2013.01); *A61N 2007/0026* (2013.01)

(58) Field of Classification Search
CPC ................ A61N 1/36031; A61N 2/006; A61N 2007/0026; A61B 5/369; A61B 5/37; A61B 5/372; A61B 5/384; A61B 5/386; A61B 5/245; A61B 5/291; A61B 5/293; A61B 5/25; A61B 5/252; A61B 5/259; A61B 5/274; A61B 5/276; A61B 5/283; A61B 5/0075; A61B 5/055; A61B 5/70; A61B 5/702; A61B 5/704; A61B 5/706; A61B 5/708; A61B 5/4064; A61B 5/4836; A61B 5/4094; A61B 5/4812
See application file for complete search history.

(56) References Cited

U.S. PATENT DOCUMENTS

| 9,198,612 | B2 | 12/2015 | Fueyo et al. | |
|---|---|---|---|---|
| 10,946,196 | B2 | 3/2021 | Weisend | |
| 2002/0082514 | A1* | 6/2002 | Williams | A61B 1/00048 600/544 |
| 2005/0070971 | A1 | 3/2005 | Fowler et al. | |
| 2005/0228461 | A1* | 10/2005 | Osorio | A61B 5/4094 607/45 |
| 2009/0259137 | A1 | 10/2009 | Delic et al. | |
| 2011/0028827 | A1 | 2/2011 | Sitaram et al. | |
| 2011/0046503 | A1 | 2/2011 | Pradeep et al. | |
| 2011/0137371 | A1* | 6/2011 | Giftakis | A61B 5/4094 607/45 |
| 2011/0201944 | A1 | 8/2011 | Higgins et al. | |
| 2011/0224572 | A1 | 9/2011 | Gilja et al. | |
| 2012/0041330 | A1 | 2/2012 | Prichep et al. | |
| 2012/0179019 | A1 | 7/2012 | Fadem | |
| 2012/0296390 | A1 | 11/2012 | Nakashima et al. | |
| 2013/0131461 | A1 | 5/2013 | Jorge et al. | |
| 2013/0184779 | A1 | 7/2013 | Bikson et al. | |
| 2014/0350634 | A1 | 11/2014 | Grill et al. | |
| 2015/0174418 | A1 | 6/2015 | Tyler et al. | |
| 2015/0374303 | A1 | 12/2015 | Gelbman et al. | |
| 2016/0048753 | A1 | 2/2016 | Sussillo et al. | |
| 2016/0206871 | A1 | 7/2016 | Weisend | |
| 2017/0087367 | A1 | 3/2017 | Weisend | |
| 2017/0333696 | A1 | 11/2017 | Shibata | |
| 2019/0073030 | A1 | 3/2019 | Lee et al. | |
| 2019/0125255 | A1 | 5/2019 | Pradeep | |
| 2020/0155061 | A1 | 5/2020 | Pradeep | |
| 2021/0290155 | A1 | 9/2021 | Pradeep | |

FOREIGN PATENT DOCUMENTS

| WO | 2018022793 | 2/2018 |
|---|---|---|
| WO | WO-2018071426 A1 | 4/2018 |
| WO | 2020106641 A1 | 5/2020 |

OTHER PUBLICATIONS

U.S. Appl. No. 16/195,634, Non-Final Rejection, dated Apr. 1, 2020, 9 pgs.
U.S. Appl. No. 16/195,634, Non-Final Office Action dated Mar. 4, 2021, 19 pgs.
Boasso, A.M., Mortimore< H., Silva, R., Aven, L. and Tyler, W.J. Transdermal electrical neuromodulation of the trigeminal sensory nuclear comples improves sleep quality and mood.
Demirtas-Tatlidede et al.: "Noninvasive Brain Stimulation in Traumatic Brain Injury", Journal Head Trauma Rehabilitation, 2012, 27(4): 274-292. Jul. 1, 2012.
Diego Oswaldo Perez Trenard, "Optimal control of non-invasive neuromodulation for the treatment of sleep apnea syndromes" Signal and Image Processing. Universite Rennes 1, 2018.
International Application Serial No. PCT/US2019/062053, Search Report and Written Opinion dated Mar. 12, 2020. pp. 12.
Lee, H.J., "Is It Possible to Have Neuromodulation Therapies to Treat Insomnia through Circadian Process Activation?" Chronobiology in Medicine pp. 49-50.
Wagner T. et al.: "Noninvasive Human Brain Stimulation", Annual Review of Biomedical Engineering, 2007, 9:527-565. Feb. 1, 2007.
International Application Serial No. PCT/US19/62053, Preliminary Report on Patentability dated Jun. 3, 2021, 8 pgs.
U.S. Appl. No. 15/290,391, Final Rejection, dated Jul. 2, 2020, 10 pgs.
U.S. Appl. No. 15/290,391, Office Action Appendix, dated Nov. 4, 2020, 2 pgs.
U.S. Appl. No. 15/290,391, Examiner Interview Summary Record (Ptol-413), dated Nov. 4, 2020, 2 pgs.
U.S. Appl. No. 15/290,391, Notice Of Allowance And Fees Due (Ptol-85), dated Nov. 12, 2020, 9 pgs.
U.S. Appl. No. 15/290,391,Examiner Interview Summary Record (Ptol-413), dated Dec. 5, 2019, 2 pgs.
U.S. Appl. No. 15/290,391, Final Office Action dated Aug. 2, 2019.
"U.S. Appl. No. 14/083,379, Final Office Action dated Jun. 7, 2017", 14 pgs.
"U.S. Appl. No. 14/083,379, Non Final Office Action dated Jan. 4, 2018", 12 pgs.
"U.S. Appl. No. 14/083,379, Non Final Office Action dated Sep. 26, 2016", 60 pgs.
"U.S. Appl. No. 14/083,379, Preliminary Amendment filed Mar. 5, 2015", 4 pgs.
"U.S. Appl. No. 14/083,379, Response filed Mar. 27, 2017 to Non Final Office Action dated Sep. 26, 2016", 13 pgs.
"U.S. Appl. No. 14/083,379, Response filed Dec. 6, 2017 to Final Office Action dated Jun. 7, 2017", 10 pgs.
"U.S. Appl. No. 15/290,391, Non Final Office Action dated Nov. 13, 2018", 17 pgs.
"U.S. Appl. No. 15/290,391, Non Final Office Action dated Dec. 19, 2019", 12 pgs.
"U.S. Appl. No. 15/290,391, Response filed Apr. 15, 2019 to Non Final Office Action dated Nov. 13, 2018", 14 pgs.
"U.S. Appl. No. 15/290,391, Response filed May 19, 2020 to Non Final Office Action dated Dec. 19, 2019", 13 pgs.
"U.S. Appl. No. 15/290,391, Response filed Aug. 29, 2018 to Restriction Requirement dated Mar. 1, 2018", 1 pgs.
"U.S. Appl. No. 15/290,391, Response filed Oct. 30, 2020 to Final Office Action dated Jul. 2, 2020", 12 pgs.
"U.S. Appl. No. 15/290,391, Response filed Dec. 2, 2019 to Final Office Action dated Aug. 2, 2019", 13 pgs.

(56) References Cited

OTHER PUBLICATIONS

"U.S. Appl. No. 15/290,391, Restriction Requirement dated Mar. 1, 2018", 5 pgs.
"U.S. Appl. No. 17/339,881, Non Final Office Action dated Aug. 4, 2022", 17 pgs.
"International Application Serial No. PCT/US2017/055950, International Preliminary Report on Patentability dated Apr. 25, 2019", 13 pgs.
"International Application Serial No. PCT/US2017/055950, International Search Report dated Jan. 25, 2018", 4 pgs.
"International Application Serial No. PCT/US2017/055950, Written Opinion dated Jan. 25, 2018", 11 pgs.
"U.S. Appl. No. 17/339,881, Final Office Action dated Dec. 29, 2022", 13 pgs.

* cited by examiner

SYSTEM FOR VARIABLY CONFIGURABLE, ADAPTABLE ELECTRODE ARRAYS AND EFFECTUATING SOFTWARE

CROSS-REFERENCE TO RELATED APPLICATIONS

This application is a continuation of U.S. patent application Ser. No. 15/290,391 filed Oct. 11, 2016, issued as U.S. Pat. No. 10,946,196 on Mar. 16, 2021 which is a continuation-in-part of U.S. patent application Ser. No. 14/083,379 filed Nov. 18, 2013, abandoned, which claims the benefit of priority to U.S. Prov. Pat. Apps. 61/796,634 filed Nov. 16, 2012, and 61/962,698 filed Nov. 14, 2013, each of which are incorporated herein by reference in its entirety.

FIELD OF THE INVENTION

The present technology relates to the use of various electrical stimulation, variably configurable and adaptable electrodes and electrode arrays, methods and software for affecting electrical communication systems that naturally occur in the brain, and for effecting various kinds of advantageous neurological intervention, such as redirecting learning processes. The various types and intensities of electrical stimulation may be adapted and arranged to amplify, or to cancel, targeted portions and functions of the brain. The technology has numerous uses, applications and embodiments.

BACKGROUND OF THE INVENTION

The application of electric fields or stimuli to the brain has been demonstrated for a variety of neurological conditions, including the treatment of psychological disorders. Attempts have been made to utilize such electrical stimuli to aid in the learning and teaching processes. However, many of the known methods involve invasive surgical procedures that carry considerable risk. While some non-invasive methodologies have begun to show promise, novel devices, systems, networks and methods are needed to address a variety of conditions and circumstances for which electrotherapies can be helpful. This is especially true in the teaching and scholarly fields, particularly as applied to personnel in the therapeutic, intelligence and military education fields.

One method for applying electrical stimulation to regions of the brain to facilitate learning processes is Conventional Transcranial Direct Current Stimulation (c-TDCS). During a c-TDCS treatment, electrodes are positioned on the head based on general knowledge about cognitive processes and the location of the relevant brain structures that are involved. For example, working memory is the cognitive process that allows us to hold information in memory for short periods of time. The working memory of a subject is one of the primary neurological requirements when looking up, e.g., a phone number and remembering that number until it is dialed. After the number is dialed, the working memory is typically cleared and the number is no longer remembered by the person. A portion of the brain in the left, frontal region, i.e., dorsal lateral prefrontal cortex (DLPFC) is reliably activated during working memory tasks as indicated by neuroimaging with, e.g., functional magnetic resonance imaging (fMRI), electroencephalography (EEG), magnetoencephalography (MEG), positron emission tomography (PET), single photon emission computed tomography (SPECT), and functional near infrared spectroscopy (fNIRS).

Thus, in a c-TDCS effort to facilitate working memory, one of the electrodes (anode or cathode) is placed over the left frontal region of the subject's brain, and typically the other will be placed on the right forehead. The c-TDCS approach generally results in 10%-20% gains in the length of retention or the number of items that can be remembered. However, the c-TDCS approach and technology is limited and inapplicable to many circumstances for several reasons, including the ones iterated below.

First, c-TDCS is an suboptimal approach to the problem of facilitating cognition as c-TDCS uses general knowledge about the brain, the brain's cognitive functions, and the task at hand to target brain stimulation. Thus, methods and systems based upon c-TDCS are optimal, only when the task at hand activates the same brain areas and utilizes the same brain functions as did many previous tasks. Hence, c-TDCS is limited or inapplicable when the details of brain function, in terms of variation between individuals and within individuals over time are considered.

Second, given that scientific endeavors try to push the frontiers of knowledge, identical tasks are rarely repeated. Thus, c-TDCS does not address the circumstances when the problem to be addressed is new. Similar disadvantages pertain when a task is more complicated than remembering a series of numbers. Decisions regarding the placement of electrodes to influence specific, task-related brain regions are always necessary in brain stimulation research and related methods to enhance human cognitive performance. With c-TDCS methods, the placement of electrodes is largely speculative.

Third, both the anode and the cathode have effects on brain activity. Placing for the anode and cathode on the head results in enhanced brain activation in regions near the anode and suppressed brain activity in regions near the cathode. The combined enhancement in some brain regions and suppression in others may have unintended consequences in terms of facilitating cognition and significantly complicates the interpretation of the extant data set. These disadvantages mean that c-TDCS is both inaccurate and inapplicable in many circumstances.

Hence, methods for locating the particular regions of the brain to be treated and devices and methods for treating these locations are desirable for the enhancement of human cognitive performance and treatment of brain disease with non-invasive brain stimulation (NIBS).

SUMMARY OF THE INVENTION

The present technology includes several methods and devices whereby neurological interventions are effected essentially by electrical NIBS-based procedures accomplished by the devices and methods described herein. These methods and devices are provided to be directed toward specific tasks, diseases, disorders and treatments. In one aspect, these devices and methods are adapted and arranged to be used on one or a plurality of subject brains for various purposes, affects and results. For instance, the devices and methods described herein provide methods for obtaining more accurate and dependable information that can be gathered from the brains of subjects and for directing electrical NIBS to enhance cognitive performance, i.e. learning processes and functions in the brain, and treating the symptoms and root causes of patients with brain disease.

Furthermore, the NIBS methods described herein are guided by advanced neuroimaging methods that quantify the differences between healthy brains and patient populations or difference across time within populations of individuals.

The described method identifies patterns of brain activity or anatomy that underlie different brain states, models the patterns of energy distribution in the brain from NIBS devices, and then applies the NIBS device to alter behavior.

For instance, electrical NIBS is the first embodiment of neuroimaging-guided non-invasive brain stimulation (ng-NIBS). However, the principles of ng-NIBS are readily expanded to include, e.g., transcranial magnetic stimulation (TMS), repetitive TMS (rTMS), pulsed electromagnetic fields (PEMF), transcranial alternating current stimulation (TACS), transcranial random noise stimulation (TRNS), time varying electrical stimulation (TVES), ultrasound brain stimulation (UBS), etc.

One method for applying NIBS is by utilizing Transcranial Direct Current Stimulation (TDCS) which generally delivers a weak current to the brain via electrodes that are affixed to the scalp of a subject. TDCS may temporarily alter brain function for a short period of time where periods of brain function alteration may typically range anywhere from, e.g., 10 to 60 minutes, where the one or more areas of the brain that are affected by TDCS are primarily dependent on the location of the electrodes placed upon the patient's scalp.

One variation of the electrode housing assembly may have one or more individual electrodes arranged in various configurations within the housing body for stimulating the underlying brain region through the patient's scalp. To facilitate the electrical communication from the electrodes to the brain, the electrodes may be housed within or surrounded by an individual cavity or channel designed to hold a medium such as electrically conductive gel (e.g., a pH buffered electrode gel) for facilitating the electrical transmission.

The electrodes are configured in circular shapes (e.g., toroid-shaped) arranged in a planar manner over the electrode housing; however, the electrodes may be formed into other shapes. The electrode housing may be fabricated from a variety of non-porous and non-electrically conductive materials such as polymers or plastics. The toroid-shaped electrodes have shown stability over the treatment time period and they do not leak errant currents on the areas surrounding the skin-electrode interface. These electrodes also maximize the edge length to thereby reduce TDCS-elicited sensations at the skin-electrode interface. Each of the electrodes may have a non-conductive material which is optionally pliable (e.g., rubber, silicone, etc.) surrounding each of the respective electrodes.

In use, the electrode housing may be positioned anywhere upon the patient's scalp in proximity to the desired region for treatment, e.g., along the side of the patient's head over the frontal, parietal, temporal, etc. region so long as the electrical stimulation from the electrodes is transmitted through the scalp and into the targeted underlying region of the brain. The region of the brain for treatment may be located using the targeting methods as described in further detail herein. Additionally, the anodes and cathodes within the electrode housing can be optionally varied or interchanged on the scalp to deliver varied combinations of anodal and cathodal current to the underlying brain depending on the electrode arrangement or pattern to enhance the ability of the treatment procedure to precisely target specific structures within the brain.

Once the targeted region of the brain has been located, the electrode housing may be positioned against the patient's head, e.g., over the frontal or parietal region, and each of the electrodes may be filled with the conductive gel (e.g., a pH buffered electrode gel) or medium to facilitate electrical transmission. The electrode housing may be secured in place against the patient's head through various mechanisms.

In addition to the electrode assembly secured to the patient's scalp, an additional electrode may be secured to a portion of the arm of the subject, e.g., along the upper arm, back, shoulder, neck, or chest. The electrode secured to the non-scalp location may also be in communication with the controller as well.

The electrode-to-head connection impedance may vary from, e.g., 400 to 40,000 ohms, and once applied this impedance may likely change over time and across subjects within the 400 to 40,000 ohm range. When a constant current stimulation is desirable and the electrodes have been desirably positioned upon the patient's head, the electrical stimulation may be applied in a ramped manner so that the current is not applied instantly but is applied at an increasing level over a specified period of time. In the event that the impedance is detected to exceed 40,000 ohm, the controller may be programmed to automatically ramp down the stimulation over a specified period of time, e.g., 10 secs. An alert or alarm may be activated and the device may be placed into a pause mode. Once treatment has been completed, the current may also be reduced at a decreasing level over a specified period of time. Ramping up and ramping down the current may help to avoid any side effects affecting the user's skin and/or brain.

The electrode housing may optionally incorporate one or more sensors and/or the controller may be programmed to monitor the impedance after the electrode housing has been applied to the patient's scalp. Before, during, and/or after treatment, the impedance may be monitored to detect for changes in the impedance value. For instance, if a high impedance is detected, the controller may be programmed to provide an alert or alarm to the user or practitioner and the device may automatically terminate the electrical NIBS and/or related functions.

The electrical stimulation may be applied to the user where the initial current, e.g., 0 mA, may be increased over a ramp up period until the treatment level has been reached. The applied electrical stimulation may be applied so that the treatment level is reached over a predetermined period of time during the ramp up period so as to avoid any potential injury to the patient's tissue. For instance, the applied current may be increased over a period of, e.g., 10 secs to 15 mins, during the ramp up period where the current may be increased at intervals of, e.g., 1 sec.

The electrical stimulation parameters may be changed or adjusted by the controller and the stimulation may be applied in a number of different modalities. For instance, the applied stimulation may be time varying in the form of sinusoidal waves having a frequency of, e.g., 0 to 10,000 Hz. Additionally, the stimulation may be adapted and arranged to allow for the combination of sinusoidal waves to produce complex, time-varying waveforms that may mimic the activity and variability of a working brain.

The electrical stimulation may be applied at the treatment level for a specified period of time over the treatment period which may range anywhere from, e.g., 0.1 mins to 60 mins, in 0.1 min increments. The treatment level may also range anywhere from, e.g., 0.1 mA to 4 mA, where the treatment level may be varied in, e.g., 0.1 mA increments. The length and intensity of the treatment may be controlled through the controller.

The practitioner may program the controller with the various treatment parameters or they may be pre-set or controllable in real time via a remotely located controller. In the event that the controller is controlled remotely, communication to the controller may be maintained through various wireless or wired modalities.

The controller may optionally include a user interface which allows for the practitioner and/or patient to interface with the controller to enable the entry and/or display of various treatment parameters or the interface may simply comprise simplified external controls, e.g., controls which turn the treatment device on/off or pauses the treatment.

In the event the treatment system incorporates a pause mode to allow the practitioner or user to temporarily pause a treatment session, stimulation may be resumed after the pause. The controller may be programmed to time out further treatment after a specified period of time to prevent usage of the device beyond limits of frequency, amplitude, latency, or locations that are considered safe or effective.

After the treatment period, the stimulation may be reduced over a ramp down period until the initial current level has been reached or until the system has shut off. Like the ramp up period, the stimulation may be reduced over the ramp down period which may range anywhere from, e.g., 10 secs to 15 mins, during which the current may be decreased at intervals of, e.g., 1 sec. The controller may be optionally programmed to prevent the sudden starting or stopping of a treatment as a safety measure and to also ensure that the ramp up period and ramp down period are sufficiently timed and stepped in intensity.

The controller may be optionally further programmed to lock-out any further treatment once a treatment session has been completed for a specified period of time, e.g., 2 hrs to 36 hrs or more. This feature can be adapted and arranged in a number of different ways to limit use of the device to safe and effective treatment intervals.

Additionally and/or optionally, the controller may be further programmed to reverse the polarity of the electrodes along the electrode housing following a treatment session to prevent corrosion of the connections of the individual electrodes.

In determining the location for placing the electrode array upon the patient's head, c-TDCS generally involves utilizing only a general knowledge about the brain, the brain's cognitive functions, and the task at hand to target brain stimulation and is thus sub-optimal in locating and treating specific regions of the brain.

All challenges associated with c-TDCS may be overcome by utilizing neuroimaging-guided TDCS (ng-TDCS) which assumes no prior knowledge of the different brain areas, cognitive processes and the task at hand. Generally, application of the ng-TDCS for treatment of the subject may involve the steps of (1) recording the subject's brain activity at different states, (2) evaluating the differences between the different recorded states, (3) virtualizing the difference image between the recorded states and modeling the placement of electrodes for NIBS to visualize the currents for the purpose of optimally influencing the activity of the brain regions that are differentially activated in distinct brain states, and then (4) stimulating the subject's brain according to the modeled image.

The recording phase of ng-TDCS empirically determines the task-related brain regions or networks that should be targeted with ng-TDCS. The recording of task related brain activity can be supported with one or more neuroimaging modalities, e.g., magnetoencephalography (MEG), electroencephalography (EEG), functional magnetic resonance imaging (MRI), positron emission tomography (PET), single photon emission computed tomography (SPECT), electrocorticography (ECOG), structural magnetic resonance imaging (sMRI), diffusion tensor imaging (DTI), magnetic resonance spectroscopy (MRS), functional near infrared spectroscopy (fNIRS), etc.

One embodiment could facilitate the transition from novice to expert. The brain activity is localized to the particular brain structure(s) that are activated in low performance states (e.g., novices) and high performance states (e.g. experts). The images of the brain activity between the low performance states and high performance states are then subtracted to produce a difference image that contains only the areas of brain activity that change between low performance and high performance states.

The ng-TDCS technique takes advantage of the fact that there are desirable brain states that lead to behaviors that are well suited to the tasks and undesirable brain states that lead to poor performance on the same tasks. Desired brain states that aide performance could be attentive, happy, expert, quick, or well rested, while comparable undesirable brain states might be inattentive, sad, untrained, slow, injured, or sleep deprived. The ng-TDCS technique uses data from, e.g., MEG, EEG, fMRI, PET, SPECT, ECOG, fNIRS, sMRI, DTI, MRS, and other technologies to record data in the desirable and undesirable brain states, and in one embodiment, maps the recorded brain activity to the structures of origin using commonly available algorithms.

The localization of brain structures is done twice, once for desirable and again for undesirable brain states. This provides the basis for comparing and contrasting the structural and functional brain states that contribute to the difference between performance with desirable and undesirable outcomes. Thereby, determining the target brain region(s) where the influence of electrical ng-NIBS could move the user from an undesired to a desired brain state. The ng-NIBS approach differs from the standard practice of electrical NIBS where neuroimaging is rarely used determine target brain structures. When no neuroimaging is performed the user must rely on often poorly founded assumptions about the electrical NIBS and the brain.

For evaluating the differences between brain states, the ng-NIBS technique calculates the target for electrical NIBS by comparing and contrasting MEG, EEG. fMRI, PET, SPECT, ECOG, fNIRS, sMRI, DT1, MRS, and other techniques from two different brain states. In one embodiment, the calculation could be made across individuals where a group of individuals with a desired brain state is compared to a group of individuals with an undesirable brain state; inattentive individuals could be compared to those who are attentive, expert individuals could be compared to novices, depressed individuals could be compared to healthy subjects, brain injured individuals could be compared to healthy individuals, individuals that perform a cognitive operation quickly could be compared to those who work more slowly. This is a "one size fits most" approach to the problem of optimizing NG-NIBS.

In yet another aspect, the present technology can employ various kinds of comparisons of various kinds of brain activities within the brain of each individual in order to determine the most advantageous locations or conformations of electrodes on the scalp. Multiple measures of brain activity in desirable and undesirable brain states are recorded in each individual, the sources are localized with standard algorithms, and the images of brain activity are subtracted to find the differences in brain activity within an individual, not a group as described above, that can be used to tailor an arrangement of scalp electrodes for optimal effectiveness in each individual. For example, no two strokes are alike, no two traumatic brain injuries are alike, and no two cases of epilepsy are alike. Thus, customized arrangements of electrodes are necessary for each individual. Further, there are individual differences in the organization of healthy brains. Thus, the application of ng-NIBS can be further optimized for cognitive enhancement, sleep aide, pain relief, and other brain functions by customized application for each individual.

Additional information derived from recorded brain activity along one or more dimensions can be used to determine optimal ng-NIBS parameters for cognitive enhancement or treatment of disease and disorder. The parameters that can be used to determine ng-NIBS type include, but are not limited to, the location, amplitude, timing, phase, frequency, and duration of one or more activations in one or more brain areas.

The recorded brain activity is used not only to understand the characteristics of brain activity at specific brain regions but also to give information about the consistency or causation of amplitude relationships, time relationships, phase relationships, frequency relationships, and the duration relationships among and across multiple brain regions in response to events in the environment that are processed by the brain.

However, the application of the ng-NIBS method to determine the optimal brain targets for electrical NIBS is both innovative and extremely useful. The ng-NIBS approach allows both functional (e.g., MEG, EEG, fMRI, tNIRS, PET, SPECT, ECOG, and MRS) and structural (e.g., sMRI, DTI) comparisons between and within subjects. Previous studies have shown that one type of electrical ng-NIBS alters both structural (DTI) by reducing radial diffusivity in white matter tracts on the stimulated side of the brain and functional activity in terms of neurotransmitter turnover (MRS) as well as local and network level brain activity (MEG, EEG).

The difference image that will identify targets for stimulation within the brain can be derived by first determining the location of electrical activity (MEG, EEG, fMRI, tNIRS, SPECT, PET, ECOG), chemical concentrations (MRS), and structures (sMRI, DTI) in the brain during desirable and undesirable brain states. Second, the brain scans for desirable and undesirable brain states are coregistered for comparing similar spatial locations in the brain. Finally, the coregistered images of brain activity, chemistry, and/or structure, in desirable and undesirable brain states are subtracted. The difference image reveals the locations of brain activity that differ functionally, chemically, or structurally between desirable and undesirable brain states.

The difference image identifies regions of the brain that differ between desirable and undesirable brain states that may become targets for stimulation with electrical NIBS. Finite element modeling of a generic head or the head of an individual subject may be used to place electrical NIBS electrodes onto the head virtually using finite element modeling (FEM). The electrodes described herein can be placed on the virtual head using FEM and can be moved to see locations in the brain that are likely to be in the current path for electrical NIBS. The position of the electrodes described herein may be placed at locations on the scalp surface as to produce maximal current density in brain regions as indicated by FEM and identified as the target for stimulation by the difference image(s) in order to specifically task- or brain state related brain activity.

In some implementations a single electrode polarity may be placed on the scalp at difference image suggested scalp location(s), e.g., either anode to enhance brain activity or cathode to suppress brain activity. The other electrode may be placed on another portion of the subject's body, e.g., the upper arm, to eliminate problems caused by the placement of both anode and cathode on the scalp. This single scalp electrode approach straightforwardly enhances or suppresses brain activity without the complicating effects of simultaneous excitation and inhibition on different areas of brain. This ng-TDCS treatment can increase learning performance by 100% rather than the 10%-20% commonly observed in c-TDCS experiments.

In another embodiment, neuroimaging methods compare brain states within individuals across time, i.e. the brain states associated with correct responses could be compared to those recorded during incorrect responses, attentive could be compared to inattentive, novice could be compared to expert, tired could be compared to wide awake. The comparison of desirable and undesirable brain state within an individual could be used to develop customized electrode arrangements for electrical NIBS in each individual.

Electrical NIBS changes not only the activity of the brain but also brain anatomy. A 2011 report (van der Merwe et al., 2011) showed that fractional anisotropy is increased primarily because of a decrease in the radial diffusivity of water in the white matter tracts of the brain. This is typically interpreted as increased myelination and/or healthier white matter. This raises many possibilities for the uses of electrical NIBS in rehabilitation and white matter diseases of the brain that occur with aging, Virchow-Robin Perivascular Spaces, deep white matter ischemia, multiple sclerosis, progressive multifocal leukoencephalopathy, post-infections encephalitis, HIV related encephalitis, radiation injury, chemotherapy neurotoxicity (chemobrain), posterior reversible encephalopathy syndrome, central pontine myelinolysis, the leukodystrophies and the adreno leukodystrophies, as well as peripheral and central nervous system damage from traumatic brain injury, concussion, chronic traumatic encephalopathy, spinal cord injury, and stroke. All of these diseases could be treated with the embodiments that do comparisons across or within individuals to identify targets for electrical NIBS in the CNS.

The idea of comparing and contrasting brain activity in two conditions or across two populations is not novel. However, the use of advanced neuroimaging techniques to quantify difference between groups of people, including diseased and healthy populations, or within individuals across time in combination with finite element modeling (FEM) and individually configurable electrode arrays to empirically guide electrical NIBS interventions is quite novel. This electrical NIBS that evaluates the differences between desired and undesired brain states has been used successfully to double the rate of learning in multiple laboratories and on multiple tasks.

DETAILED DESCRIPTION OF THE INVENTION

According to the many and various embodiments of the present technology, the present disclosure provides, inter alia, various devices, methods, networks and systems for providing therapeutic and/or beneficial cranial electrostimulation. Accordingly, the present disclosure provides methods, systems, software and apparatus that utilize a combination of real time brain functional monitoring and non-invasive electrical and/or magnetic trans-cranial brain stimulation to modify the brain function as exhibited in individual and group activities.

The present technology includes several methods and devices whereby neurological interventions are effected essentially by electrical NIBS-based procedures accomplished by the devices and methods described herein. These methods and devices are provided to be directed toward specific tasks, diseases, disorders and treatments. In one aspect, these devices and methods are adapted and arranged to be used on one or a plurality of subject brains for various purposes, affects and results. For instance, the devices and methods described herein provide methods for obtaining more accurate and dependable interventions based on information that can be gathered from the brains of subjects and for directing learning processes and functions in the brain and treating the patients accordingly.

One method for applying electrical NIBS is by utilizing Transcranial Direct Current Stimulation (TDCS) which generally delivers a weak constant current to the brain via electrodes that are affixed to the scalp of a subject. Electrical NIBS can also take the form of alternating current, randomly varying currents, temporally patterned currents, or combinations of the aforementioned. Electrical NIBS may be applied for various lengths of time (typically 10-60 minutes) to temporarily alter brain function. Electrical NIBS can alter the functions of one or more areas of the brain that are primarily dependent on the location of the electrodes placed upon the subject or patient's scalp.

Electrodes

Conventional TDCS (c-TDCS) units are large, boxy, table-top devices which are provided with multiple external controls and are suitable for laboratory use but problematic for the dissemination and use of the technology to greater numbers of people. In one aspect, the TDCS systems described herein may comprise a small, portable, programmable TDCS unit that may be adapted and arranged to provide one or more programmable functions. Various aspects of the systems are designed to enhance the safety and usability of the product by many people.

Figure 1A:
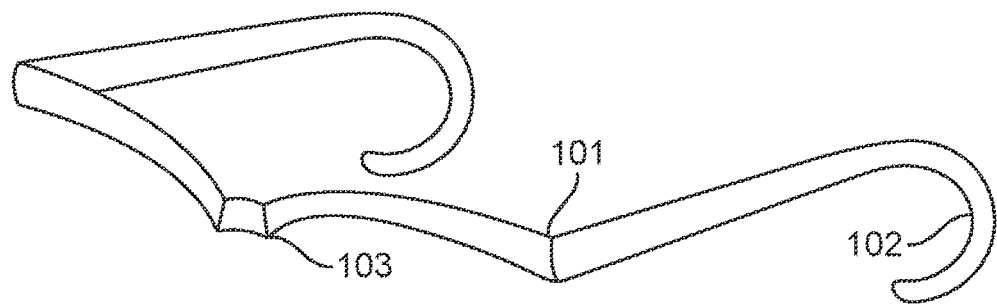
FIGS. 1A and 1B show perspective and end views of one variation of headgear for supporting a magnetic stimulation delivery system upon a patient's head for applying non-invasive brain stimulation (NIBS).
Figure 1B:
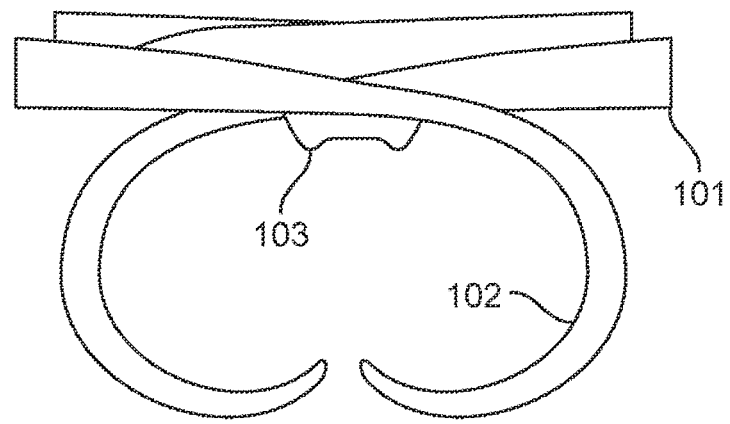

The application of TDCS may be used to change (e.g., for a short period of time) the way the brain of a subject works. TDCS applied to the head of a subject accomplishes this by delivering a very weak electrical current through the scalp and into the brain. One method for applying the TDCS may include securing one or more electrodes to the scalp by a number of different modalities. For instance, FIGS. 1A and 1B show perspective and end views of one variation of headgear 101 which can be used to facilitate placement of the one or more electrodes relative to the patient's head. The headgear 101 shown may be configured to be worn upon the patient's head like a pair of glasses where the headgear 101 may have a frame supported by two stabilizing ear loops 102 and a nose bridge 103. Once folded, the headgear 101 may be configured for compact storage, as shown in FIG. 1B, where the ear loops 102 may be folded relative to the nose bridge 103.

Figure 2A:
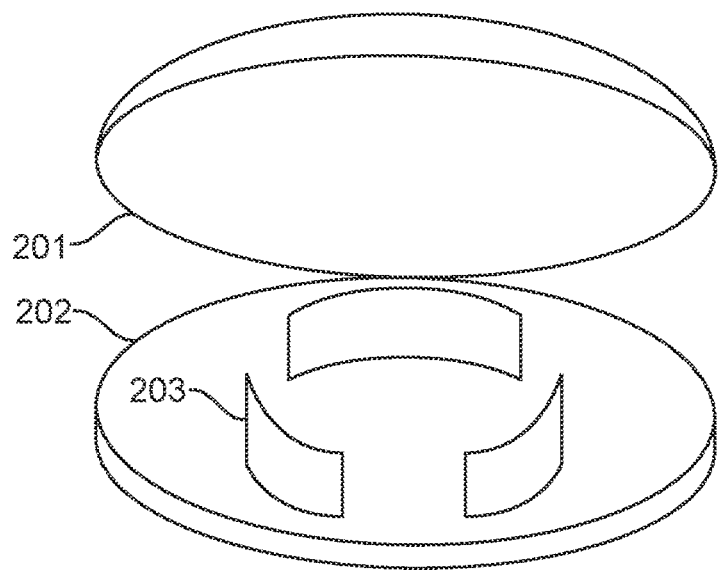
FIGS. 2A and 2B show perspective views of one variation of a portable compartment for storing various components, e.g., headgear, electrical stimulation delivery system, electronics, battery, etc. of the headgear of FIGS. 1A and 1B.
Figure 2B:
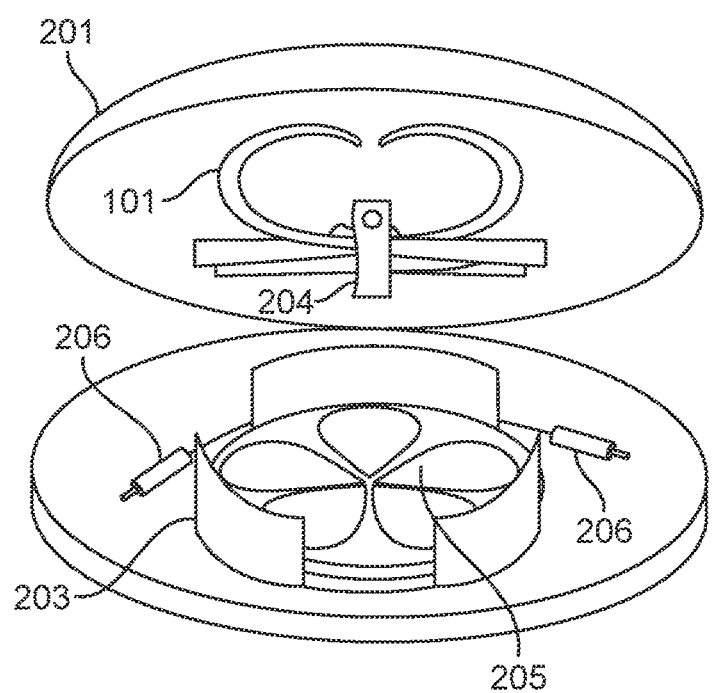

FIG. 2A illustrates a perspective view of an optional storage housing having a top lid 201 and bottom lid 202 with features or projections 203 which define a receiving channel or region for holding various components of the TDCS system, e.g., headgear, electrode assembly, electronics, power supply, etc. FIG. 2B illustrates a perspective view of various components of the TDCS system positioned within the storage housing. For instance, the headgear 101 may be folded and secured via a strap 204 upon the top lid 201 while an electrode assembly 205 having interface plugs 206 may be stored within the feature 203.

Figure 3A:
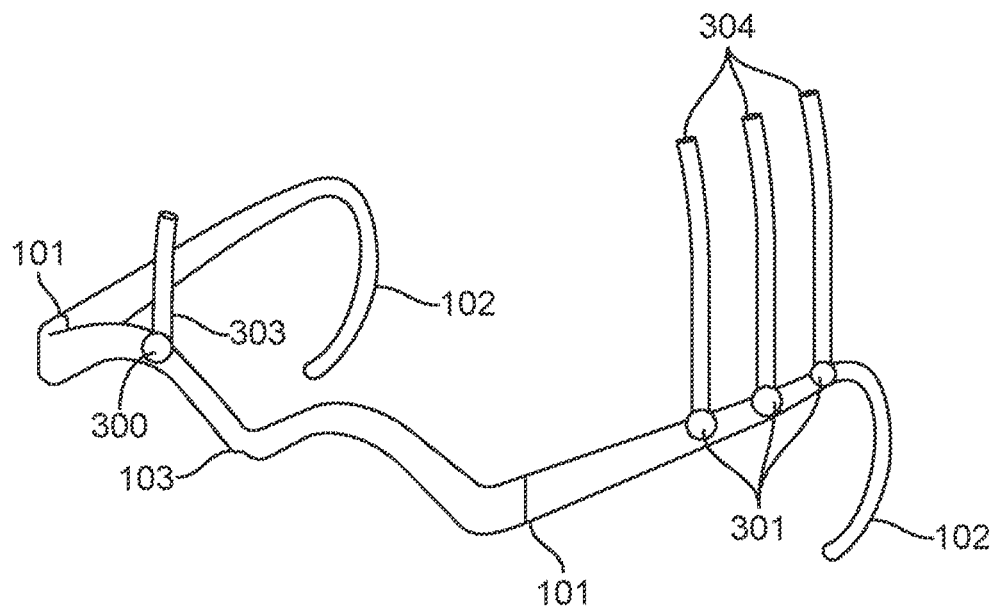
FIGS. 3A and 3B show perspective and end views of another variation of headgear configured to support a magnetic stimulation delivery system relative to the patient's head.
Figure 3B:
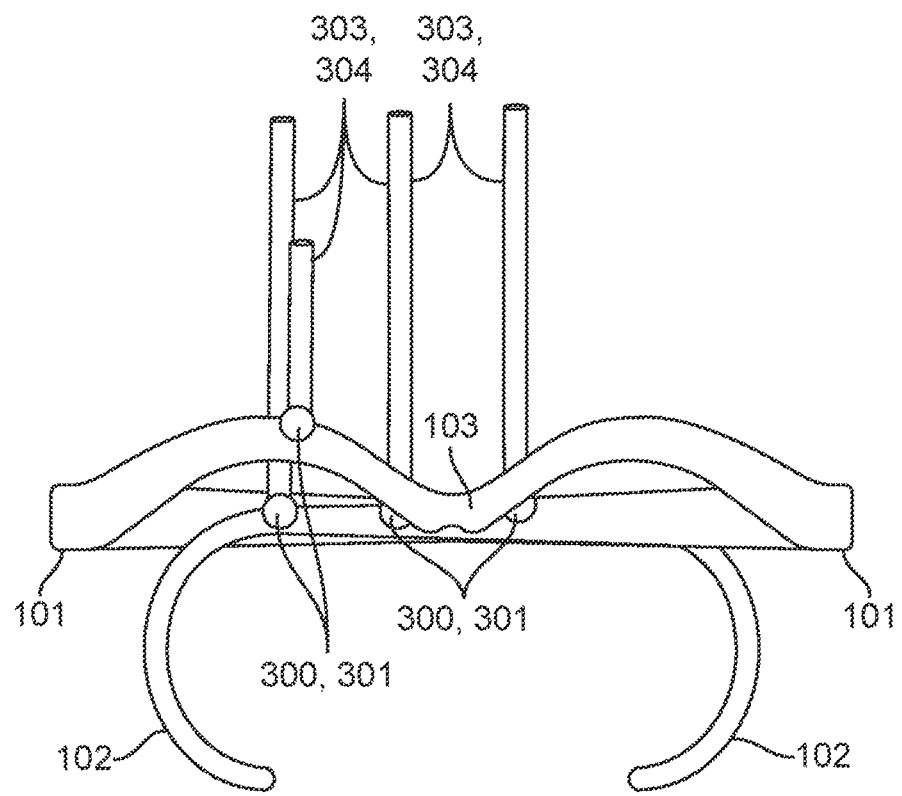

FIGS. 3A and 3B show perspective and end views of another variation of headgear which is configured to facilitate the positioning of the one or more electrodes relative to the patient's head. This variation may include headgear 101 frame supported by two stabilizing ear loops 102 and a nose bridge 103, as previously described. Additionally, this variation may further incorporate one or more hinged joints 300, 301 which connect to corresponding stanchions 303, 304 which may extend from the joints and away from the frame such that the stanchions 303, 304 are suitably positioned relative to the patient's head for holding electrode or electrode array against selected regions of the scalp. Each of the stanchions 303, 304 may be configured to be uniform in length or they may be varied depending on the region of the scalp where the electrode is to be positioned. Moreover, one or more of the stanchions 303, 304 may be adjustable in length to allow for variability of electrode positioning. Furthermore, one or more of the stanchions 303, 304 may be curved or angled to allow for additional variability in electrode positioning.

Figure 3C:
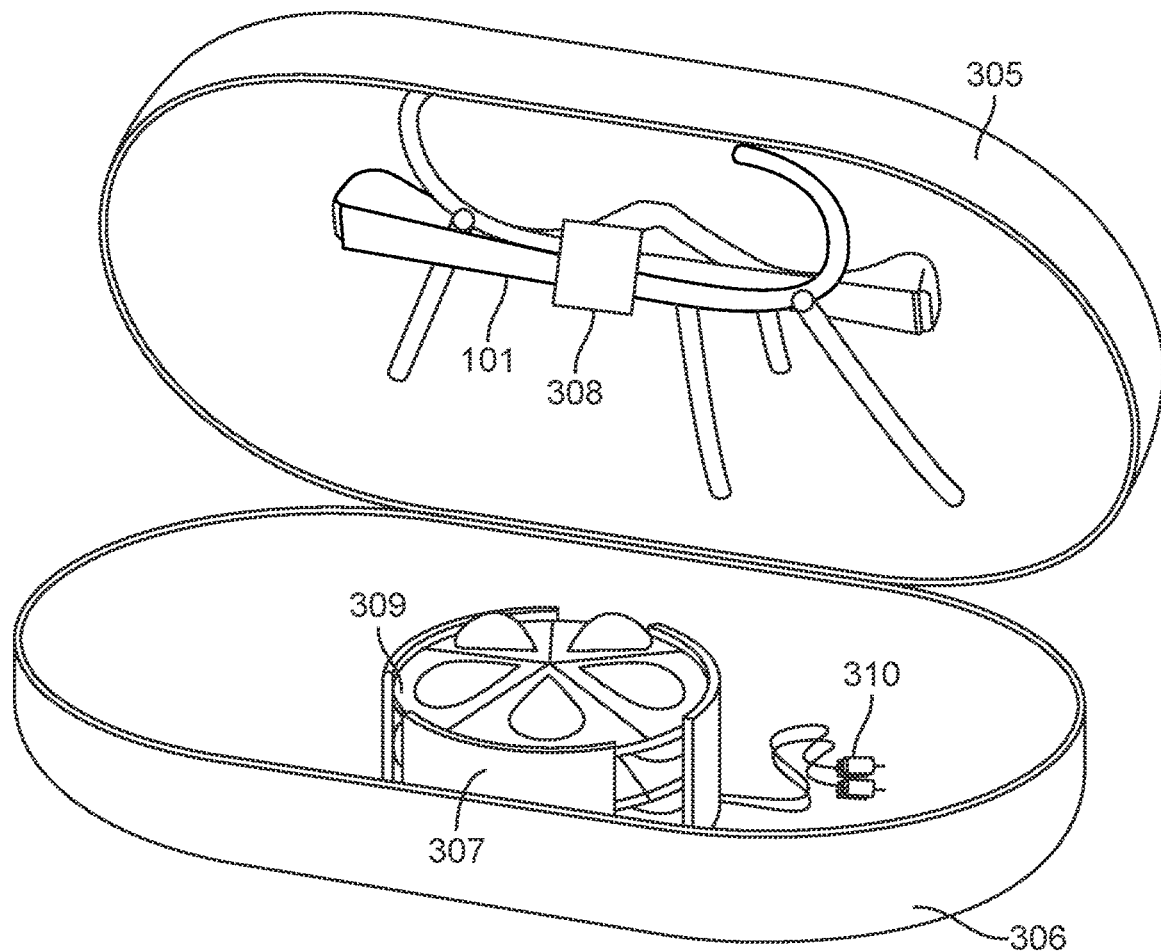
FIG. 3C shows a perspective view of another variation of a portable compartment for storing the headgear of FIGS. 3A and 3B.

When the stanchions 303, 304 are not in use such as when the headgear is stored, the stanchions 303, 304 may be folded via the hinged joints 300, 301 to allow for the stanchions 303, 304 to be folded for storage. FIG. 3C shows a perspective view of another variation of the storage housing having a top lid 305 and bottom lid 306 with features or projections 307 which define a receiving channel or region for holding various components of the TDCS system, as similarly described above. This variation illustrates an example of the headgear of FIG. 3B secured to the top lid 305 via a strap 308 and the electrode assembly 309 with interface plugs 310 stored within the receiving channel or region of the bottom lid 306.

Figure 4A:
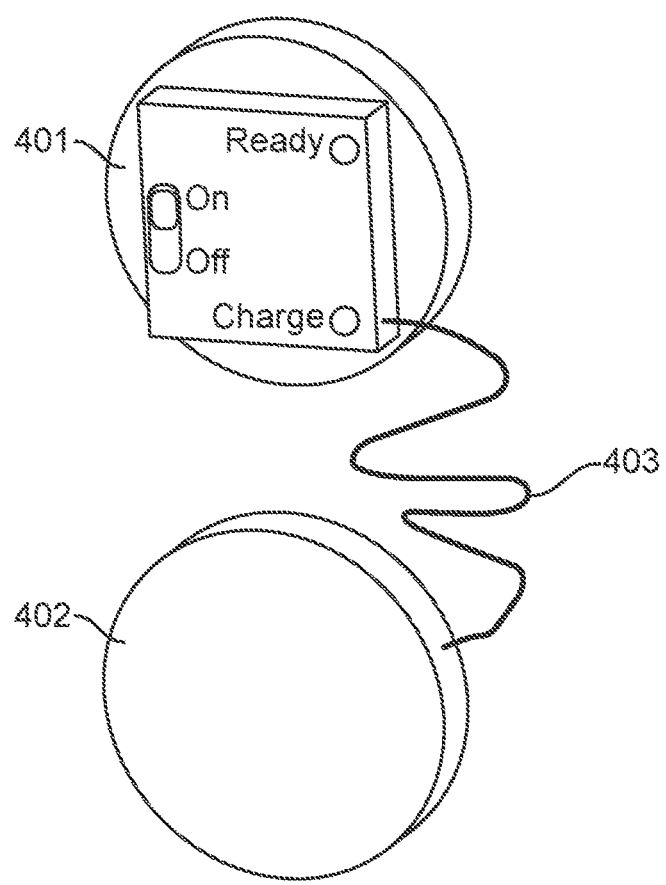
FIG. 4A shows a perspective assembly view of various components of the electrical stimulation delivery system.

FIG. 4A shows a perspective assembly view of some of the various components of the magnetic stimulation delivery system which may be incorporated into the TDCS system. A controller 401 may have a user interface for setting various delivery stimulation parameters, power actuator, one or more various indicators or alarms for alerting the user, etc. One or more wires or cables 403 may connect the controller 401 to the electrode housing 402 which may be secured to the patient's head.

The controller 401 may be powered by an external power supply or it may optionally incorporate an internal battery either within the controller 401 or separately attached. The controller 401 may thus be programmed to monitor the battery charge level to ensure that the device is capable of completing the treatment stimulation at the same charge level. One or more alerts or alarms may be included in the controller 401 to provide an indication of charge level or the information may be provided on a user interface.

Figure 4B:
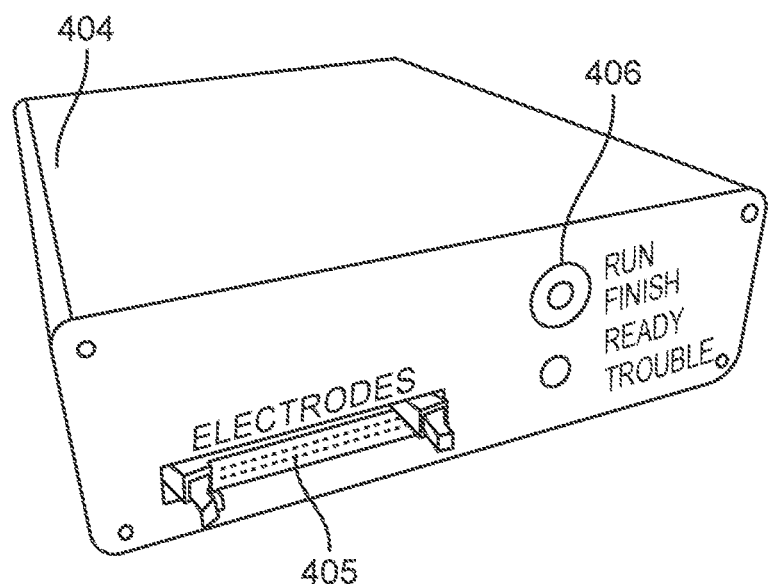
FIG. 4B shows a perspective view of a controller to which the electrode assembly may be connected.

Another variation of the controller 404 is illustrated in the perspective view of FIG. 4B. The housing of the controller 404 may contain the electronics and processor as well as power supply. The electrode assembly may be coupled to the controller 404 via a connector 405 and one or more control inputs 406 may also be incorporated into the controller 404.

Figure 5A:
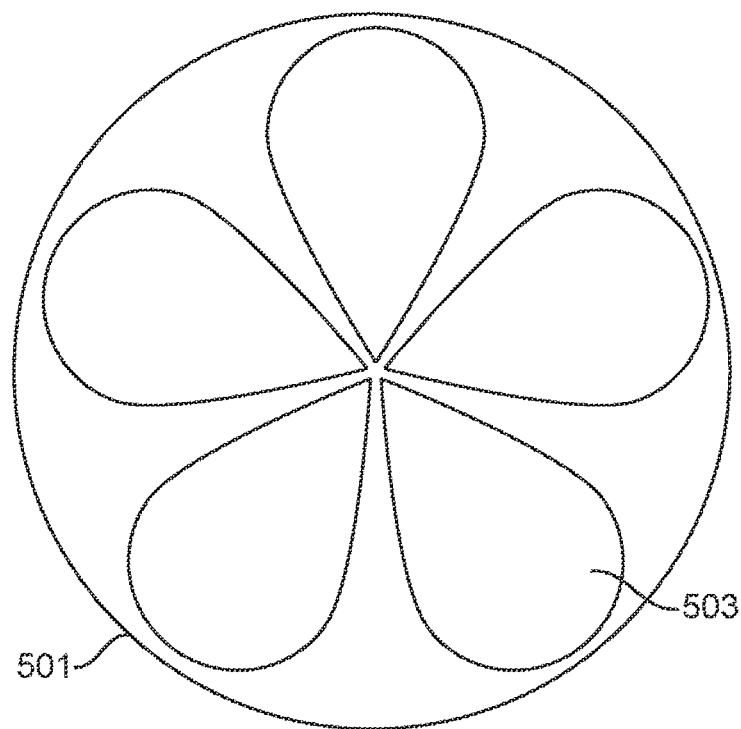
FIGS. 5A and 5B show top and side views of one variation of the electrical stimulation delivery electrode housing.
Figure 5B:
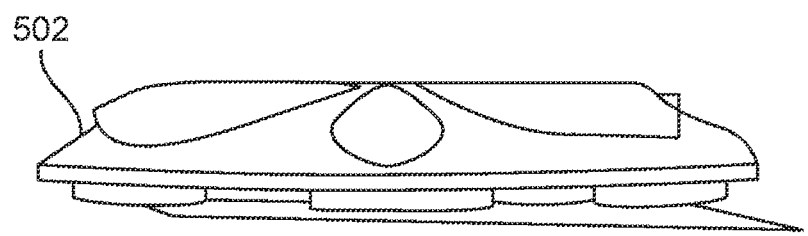

One variation of the electrode housing assembly 501 may be seen in the top and side views shown respectively in FIGS. 5A and 5B. In this variation, the electrode housing 501 may have one or more individual electrodes 503 arranged in various configurations within the housing body 502 for stimulating the underlying brain region through the patient's scalp. To facilitate the electrical communication from the electrodes to the brain, the electrodes may be housed within or surrounded by an individual cavity or channel designed to hold a medium such as electrically conductive gel (e.g., a pH buffered electrode gel) for facilitating the electrical transmission.

Figure 6A:
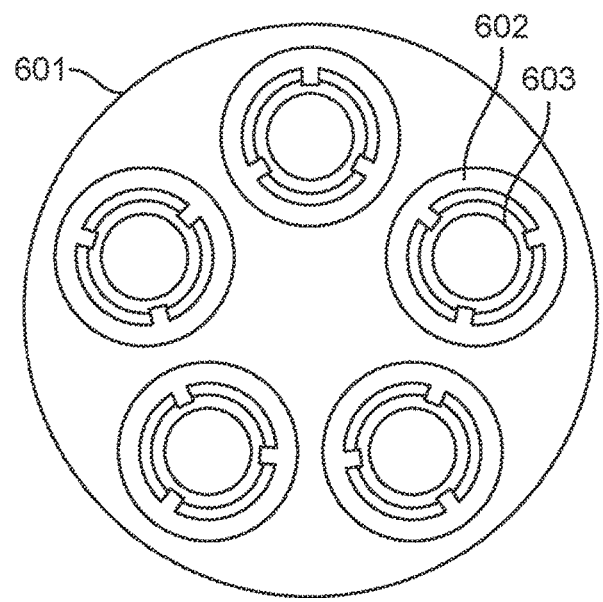
FIG. 6A shows a bottom view of one variation of the electrode housing illustrating the electrode configuration.

For instance, FIG. 6A shows a bottom view of the electrode housing 601 having a bottom surface over which the individual electrodes 603 may be arranged. The electrodes shown are configured in circular shapes (e.g., toroid-shaped) arranged in a planar manner over the electrode housing 601; however, the electrodes 603 may be formed into other shapes. The electrode housing 601 may be fabricated from a variety of non-porous materials such as polymers or plastics. The toroid-shaped electrodes have shown stability over the treatment time period and they do not leak errant currents on the areas surrounding the skin-electrode interface. These electrodes also maximize the edge length to thereby reduce electrical NIBS-elicited sensations at the skin-electrode interface. Each of the electrodes 603 may have a non-conductive material 602 which is optionally pliable (e.g., rubber, silicone, etc.) surrounding each of the respective electrodes 603. As further illustrated in the respective top and bottom views of FIGS. 6B and 6C, each electrode 603 may be configured in a circular shape which defines an opening 604 through and which is electrically coupled to a respective wire 606.

With the electrodes positioned along the bottom surface, the non-conductive material 602 may surround the electrode 603 and extend from the bottom surface to form a cavity or channel 605 having a depth of about, e.g., 4 mm, which may be optionally filled with a sufficient volume of a conductive gel (e.g., a pH buffered electrode gel) or medium to facilitate transmission of the electrical stimulation into the underlying scalp. The opening 604 in the center of the electrode 603 and the air spaces around the electrodes 603 are desirable for access to the skin surface to ensure a low impedance interface between skin and electrode.

Figure 6B:
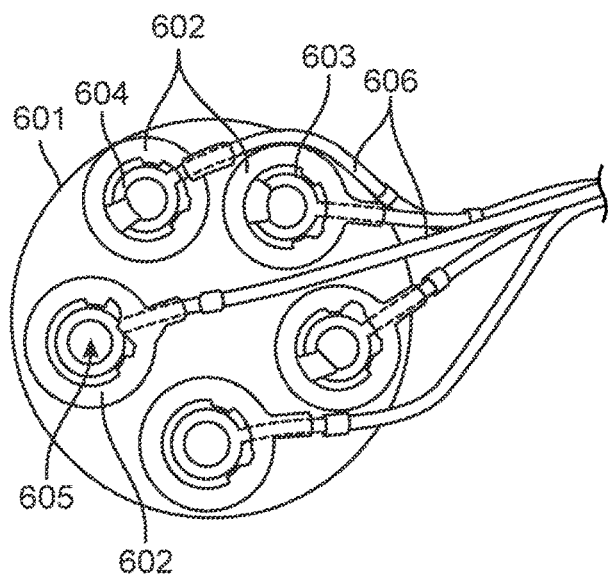
FIGS. 6B and 6C show top and bottom views of the electrode housing with the wire assembly.
Figure 6C:
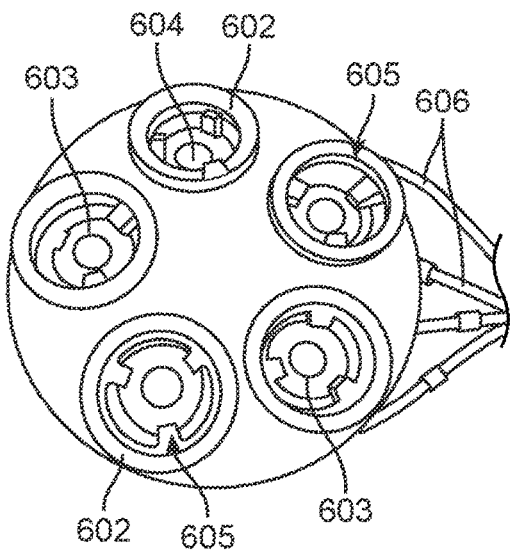

The variation shown in FIGS. 6B and 6C illustrate five electrodes 603 which are arranged in a uniform circular pattern over the electrode housing 601. However, other variations may have the electrodes 603 arranged in other patterns as needed. Moreover, the electrode housing 601 may be designed to be portable so that the housing has a dimension of, e.g., 1 cm×1 cm up to 4 cm×4 cm or greater, and a height of, e.g., up to 4 cm.

In use, the electrode housing 601 may be positioned anywhere upon the patient's scalp in proximity to the desired region for treatment, e.g., along the side of the patient's head over the frontal, parietal, temporal, etc. region so long as the electrical stimulation from the electrodes is transmitted through the scalp and into the targeted underlying region of the brain. The region of the brain for treatment may be located using the targeting methods as described in further detail herein. Additionally, the anodes and cathodes within the electrode housing 601 can be optionally varied or interchanged on the scalp to deliver varied combinations of anodal and cathodal current to the underlying brain depending on the electrode arrangement or pattern to enhance the ability of the treatment procedure to precisely target specific structures within the brain.

Figure 7A:
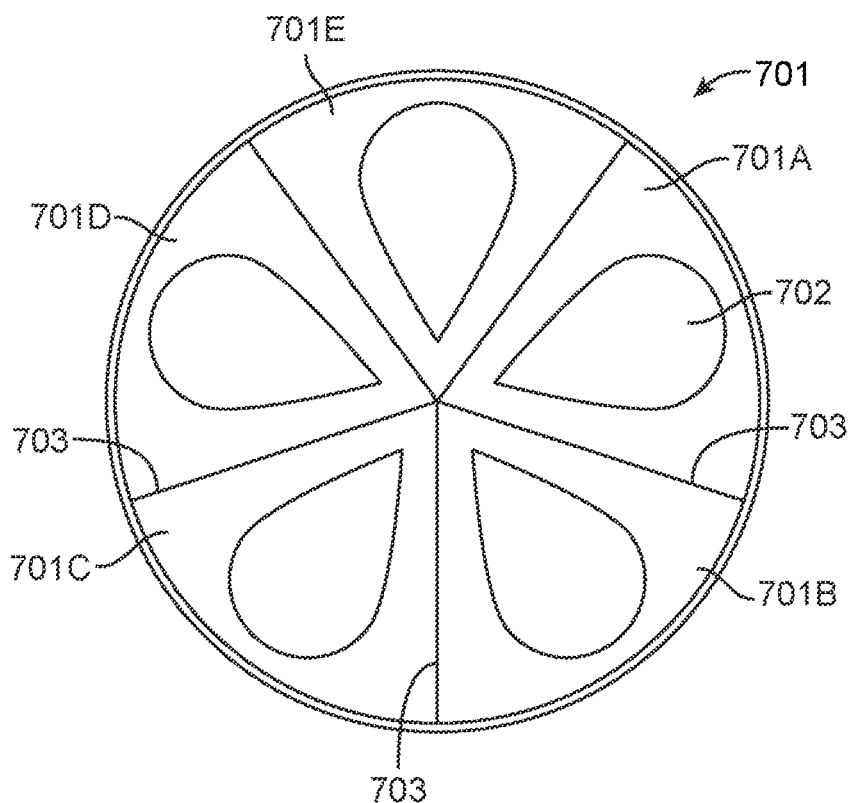
FIGS. 7A to 7C show top, perspective, and side views of another variation of the electrode housing where the assembly may be comprised of electrode components which are reconfigurable relative to one another.
Figure 7B:
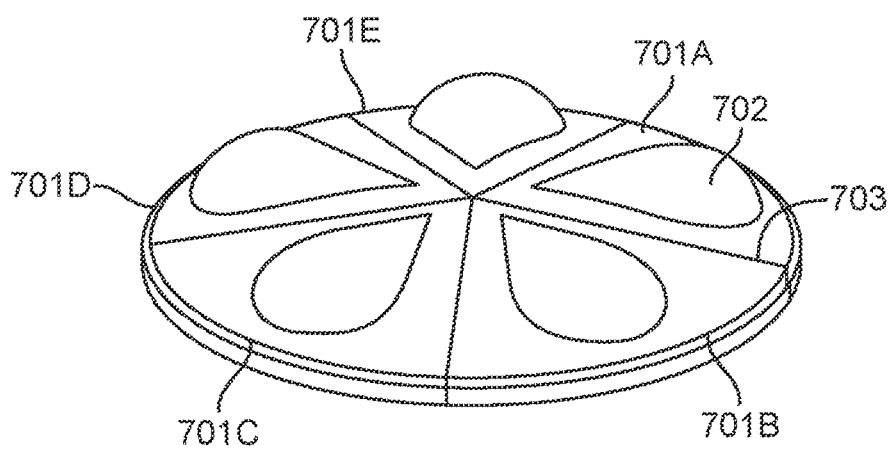
Figure 7C:
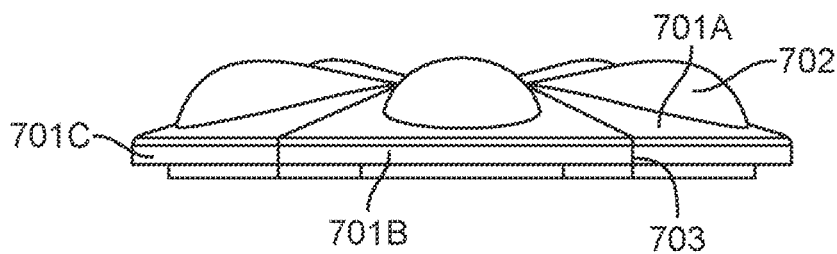

Another variation of the electrode housing is shown in the top, perspective, and side views of FIGS. 7A to 7C which illustrate an electrode housing 701 which is formed by several individual electrode components 701A to 701E which are attachable to one another in various configurations. In the variation shown, each of the electrode components 701A to 701E may have a corresponding electrode 702 and the electrode component may be formed to have uniform circular sector shape which collectively together form a circular electrode housing 701. The electrode components may be attachable to an adjacent electrode component along a component interface 703 via any number of securement mechanisms. Accordingly, the electrode housing 701 with each of the electrode components 701A to 701E may be used as an electrode assembly when positioned in proximity to the scalp.

Figure 7D:
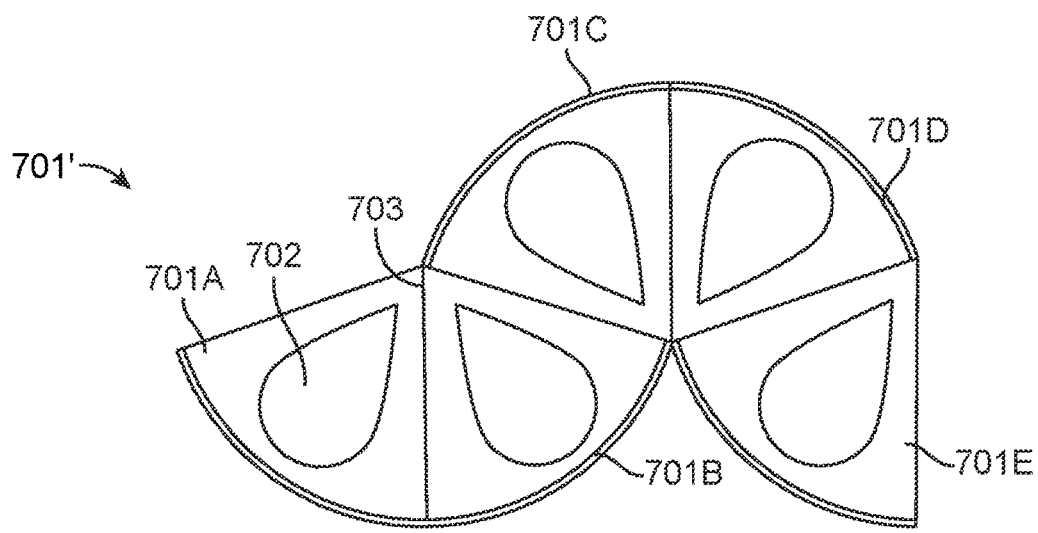
FIGS. 7D to 7F show top views of various configurations in which the individual electrode components may be reconfigured into alternative patterns.
Figure 7E:
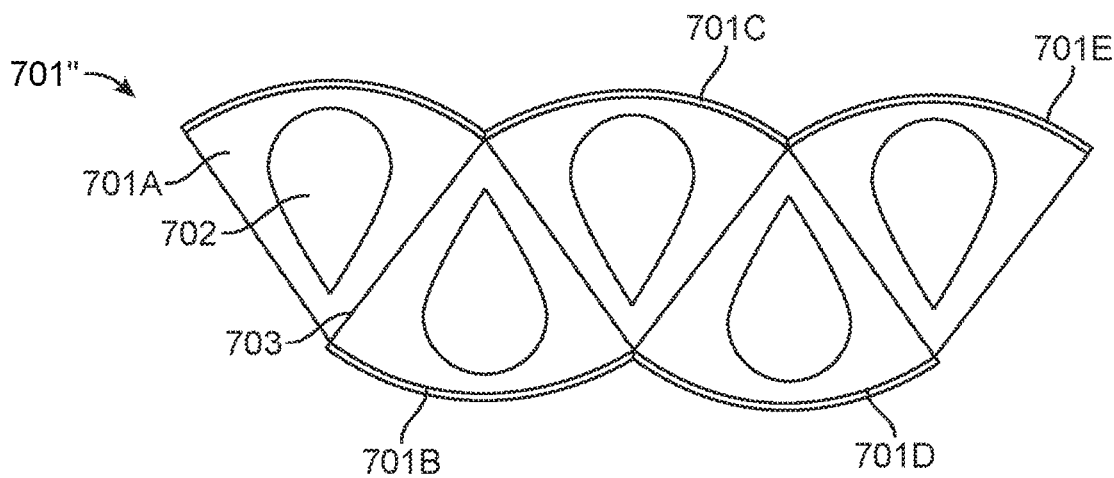
Figure 7F:
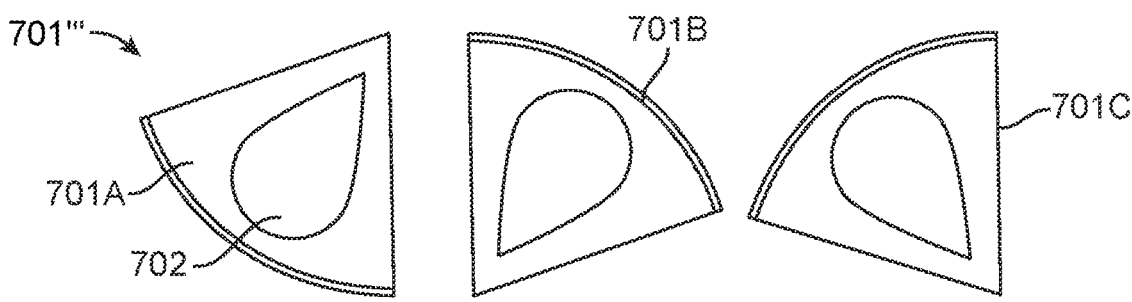

Alternatively, one or more portions of the electrode components 701A to 701E may be separated and rearranged relative to one another to form different configurations for positioning in proximity to the scalp for treatment. FIG. 7D shows a top view of one alternative arrangement 701' in which components 701C, 701D, 701E may be attached to component 701B in a reversed configuration. FIG. 7E shows another variation 701" where each of the electrode components may be attached to an adjacent component in an alternating pattern and FIG. 7F shows yet another variation 701''' where individual components may be separated and used individually. These variations are intended to be illustrative of potential arrangements and other variations are intended to be included within the scope of this description.

Figure 7G:
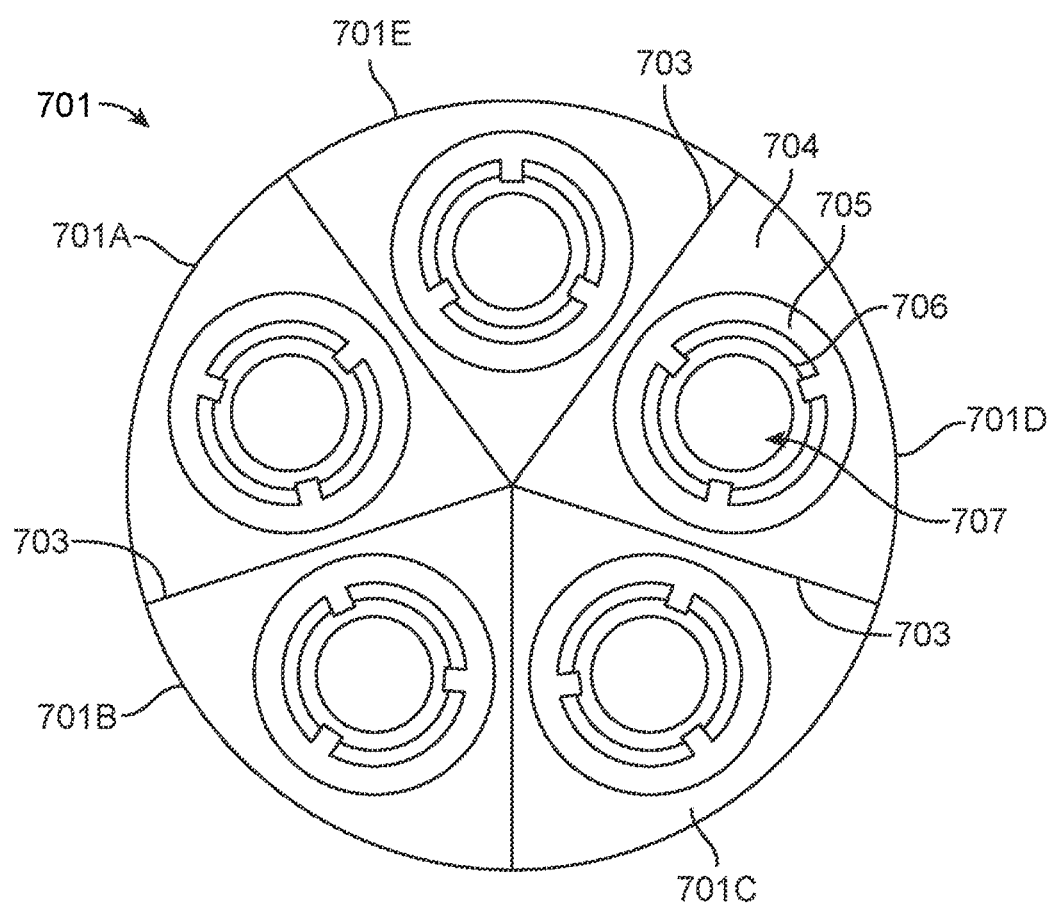
FIG. 7G shows a bottom view of the reconfigurable electrode housing illustrating the electrode configuration.

FIG. 7G shows a bottom view of the electrode housing 701 when formed in a circular configuration and having a bottom interface surface 704 over which the individual electrodes 706 may be arranged. The electrodes 706 shown are configured in circular shapes (e.g., toroid-shaped) arranged in a planar manner with a non-conductive material 705 surrounding the electrode 706 and extending from the bottom surface to form a cavity or channel 707.

The designing and configuring of the individual electrodes and arrays of electrodes can be accomplished by applying finite element modeling (FEM) to data gathered regarding the brain, scalp, skull and associated tissues. In this aspect, the finite element model can be adapted and arranged to function as a guide with respect to the influence of the electrical NIBS on one or more portions, regions or areas of one or more target brain regions. With the gathered data, and with the assistance of finite element analysis, the relative configuration(s) and design(s) of the electrodes and electrode arrays can be effected with respect to various brain tissues in terms of, for example, the spatial distribution, polarity, and intensity of the excitation or inhibition delivered via NIBS. The combination of these systems, methods, devices, components and elements of the present technology are directed toward an efficient and effective step or activity of stimulating one or more target brains with electrical NIBS. As another advantage, one or more of the polarity, intensity, and spatial distribution of stimulation can be programmed into the devices and arrays described herein to produce maximal influence (excitation or inhibition) at the target sites.

Figure 8A:
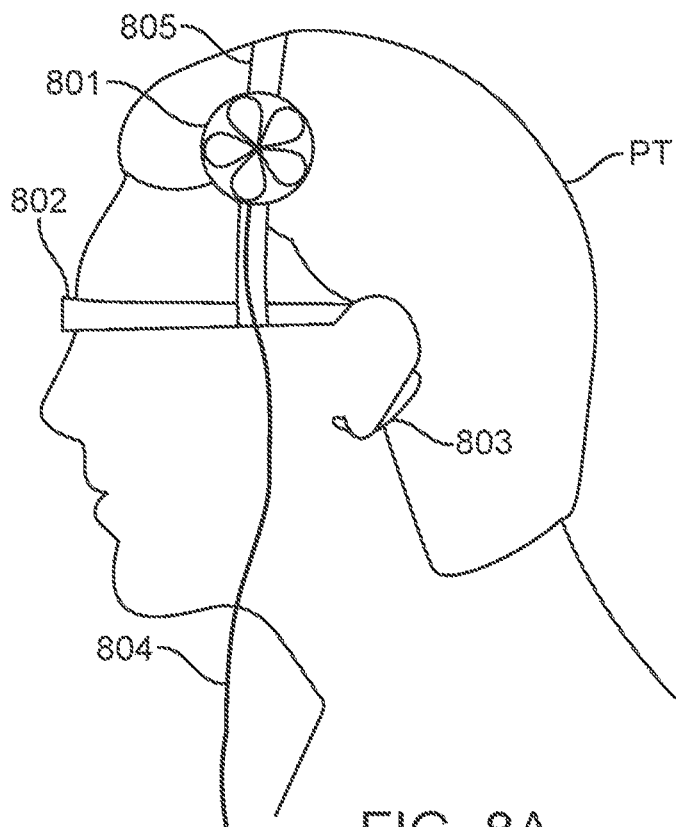
FIGS. 8A and 8B show variations for positioning the electrode housing upon the head of a patient utilizing headgear.

Once the targeted region of the brain has been located, the electrode housing 801 may be positioned against the patient's head PT, e.g., over the frontal or parietal region as shown in the side view of FIG. 8A, and each of the electrodes may be filled with the conductive gel (e.g., a pH buffered electrode gel) or medium to facilitate electrical transmission. The electrode housing 801 may be secured in place against the patient's head through various mechanisms, e.g., the headgear 802 shown secured to the patient's head via the loops 803 and optional band 805. The electrode housing 801 may be seen with the electrical wires or cables 804 coupled to the housing 801 and to a controller.

Optionally, the electrode housing 801 may incorporate a pressure activated switch which requires the user or practitioner to affirmatively press the electrode housing 801 against the patient's scalp. Once the pressure switch is activated, the controller 501 may be programmed to automatically begin the intervention or treatment stimulation.

Figure 8B:
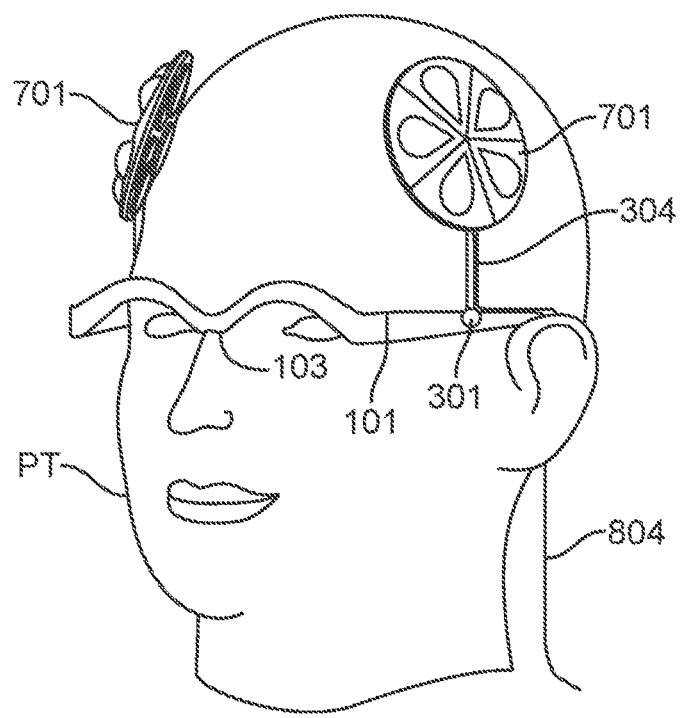

FIG. 8B shows a perspective view of the patient PT with headgear 101 with the one or more stanchions 304 extending from the frame. In this example, the electrode housings 701 in its circular configuration are attached to the end of stanchions 304 for positioning relative to the patient's scalp.

In other variations, the electrode housing 701 may be rearranged and/or separated, as described above, and secured to one or more stanchions 304 as desired for positioning over various regions of the scalp.

Figure 9A:
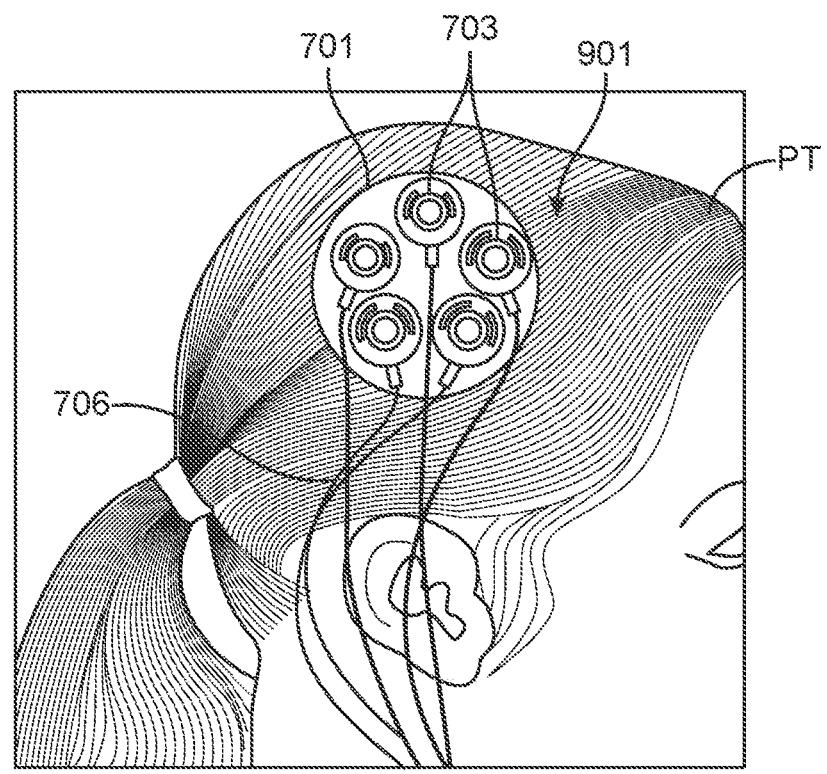
FIG. 9A shows another view of the electrode housing positioned upon the patient's head for targeting predetermined regions of the brain.

FIG. 9A shows another side view of another variation of the electrode housing 701 positioned upon the patient's PT scalp at a treatment location 901, e.g., over the frontal or parietal region (depending upon the region of the brain to be stimulated). The electrodes 703 may be seen arranged upon the electrode housing 701 in a uniform circular pattern (e.g., five-electrode array) with each electrode 703 being surrounded by the corresponding non-conductive material 702. Such an arrangement may be suitable for delivering the stimulation to a focal area of the brain. The cavity or channel 705 formed around each electrode 703 may be optionally filled with a conductive gel or medium, as described herein, to facilitate electrical contact with the underlying scalp for transmission of the stimulation signals into the brain regions below.

Figure 9B:
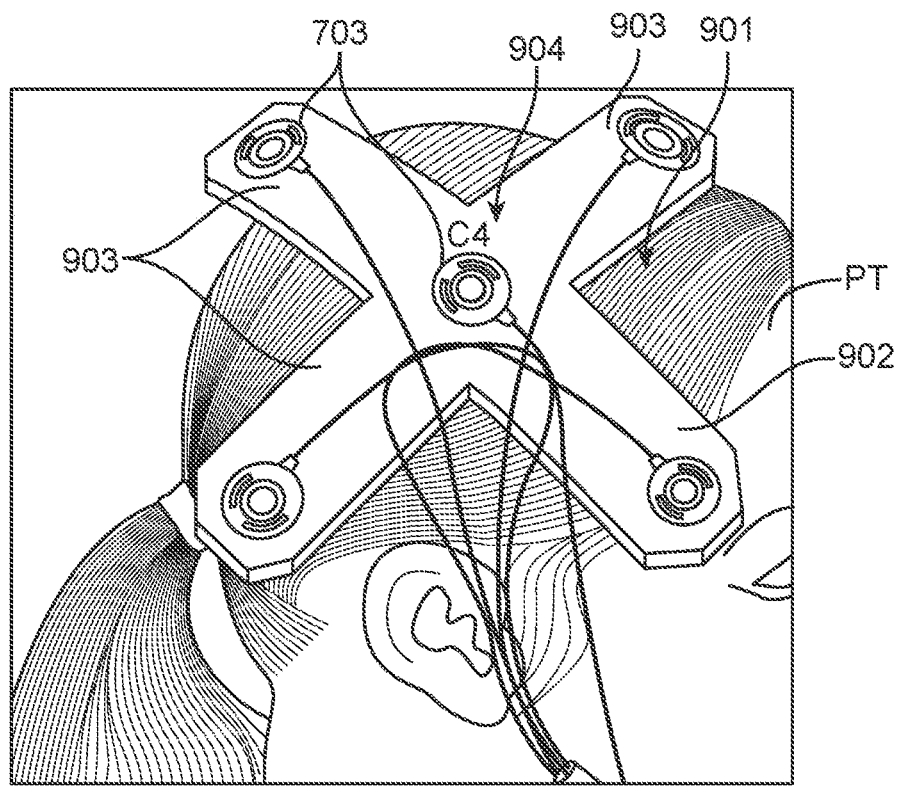
FIG. 9B shows another variation of the electrode housing for positioning relative to the patient's head.

FIG. 9B shows another variation of an electrode assembly 902 which is formed into a cross or X-shaped pattern (e.g., five-electrode array). While the electrode pattern shown in FIG. 9A was arranged in a compact pattern where each electrode 703 was positioned adjacent to one another in a circular arrangement, the arm members 903 of the electrode assembly 902 shown in FIG. 9B has its arm extending from a common intersection 904 such that the intersection 904 is centered over the treatment location 901 and the arm members 903, shown in this example as four arms extending perpendicularly relative to on another, extend over different regions of the patient's head so as to position their respective electrodes 703 at corresponding different regions of the brain. An electrode 703 may be positioned near or at the terminal end of each arm member 903 as well as near or at the intersection 904 and each of the electrodes 703 may be configured to incorporate the non-conductive material 702 for forming the cavity or channel, as previously described. The electrode assembly 902 may be secured against the patient's scalp using any of the methods described and while the arm members 903 are shown to have a uniform length, one or all of the arm members 903 may be varied in length depending upon the region of the brain to be stimulated. Such an arrangement may be suitable when delivering the stimulation over a relatively wider area of the brain rather than a focal area.

In addition to the electrode assembly secured to the patient's scalp, an additional electrode may be secured to a portion of the arm, chest, back, or neck of the subject, e.g., along the upper arm. The electrode secured to the arm may also be in communication with the controller 501 as well.

Controller

Generally, the controller may be used to drive, e.g., 24 independent channels, where each channel provides an independent current source across an electrode pair where the voltage level is controlled by an arbitrary waveform that is input into the controller, e.g., read from flash memory or other storage. The stored treatment data may comprise at least one arbitrary waveform that determines a number of different treatment parameters, e.g., frequency, amplitude, latency, location, and duration of the stimulation. The start of any operation of the system may be based on an external trigger event and the maximum voltage levels as well as time duration for stimulation may be controlled prior the start of any stimulation. That is, the maximum voltage for each channel may be determined at the beginning of the stimulation based, at least in part, on a measured impedance value in each channel so as to inhibit or prevent a relatively high current from being delivered to the subject. Hence, the current and voltage across each electrode may be monitored individually and each channel may drive an arbitrary waveform independently of one another. Moreover, because the system allows for the controller to select either bi-polar or single-ended outputs, the selection of a bi-polar output enables the use of a floating ground which allows for any arbitrary channel to be grounded and thus allows for the delivery of any desired input waveform.

Furthermore, with respect to the trigger event, the controller may be configured to receive multiple trigger inputs for responses to neuroimaging or behavioral data individually or in combination with or without Boolean logical responses to brain and behavioral state of the subject. In particular, the multiple trigger inputs for responses may be with respect to brain or behavioral state of a collocated or remotely located individual.

Figure 10:
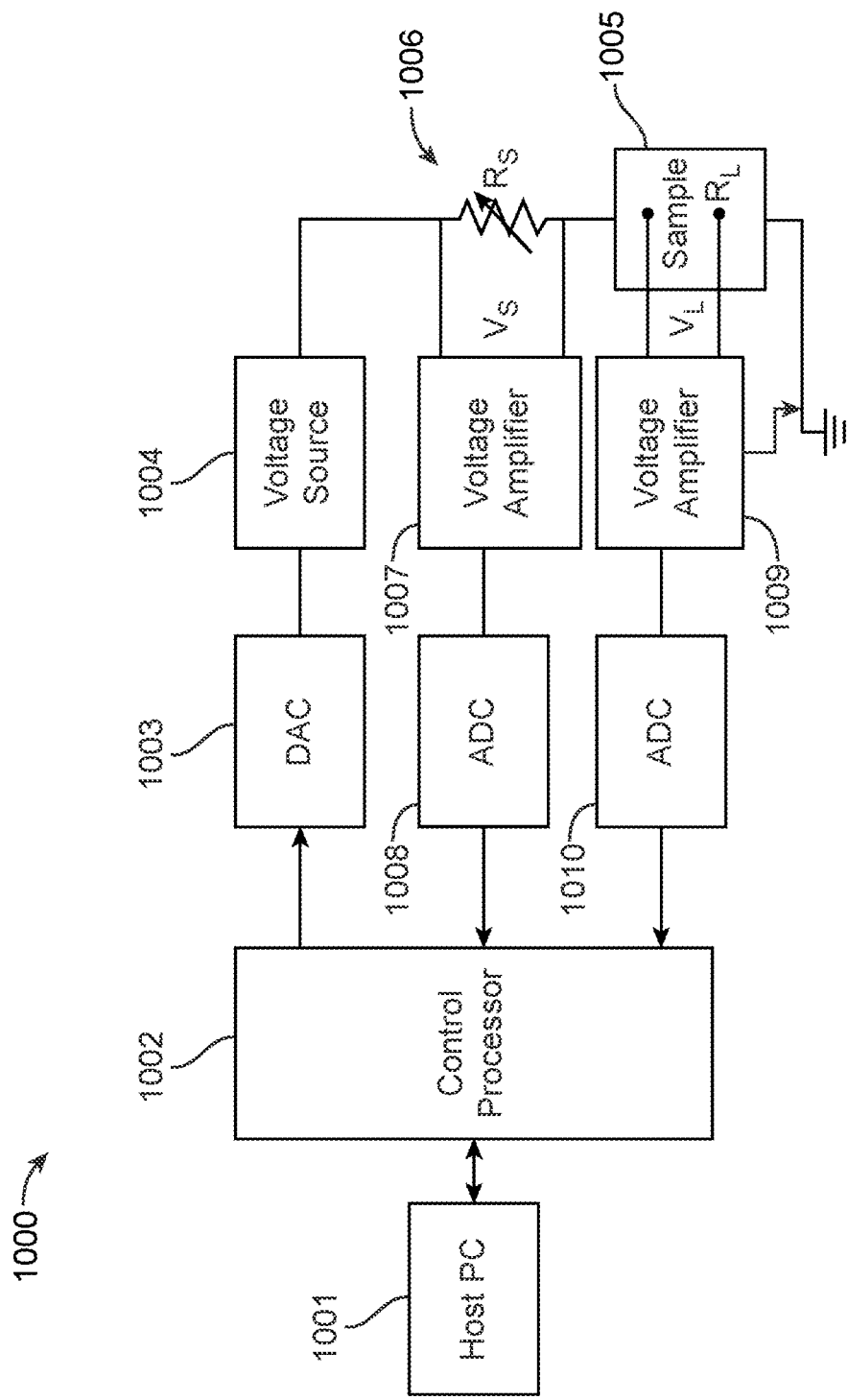
FIG. 10 shows a schematic illustration of a system block diagram for a 1-channel variation in which each channel provides an independent current source across two electrodes.

As the current is driven across the electrodes the current, voltage, and an open circuit detect circuit may monitor the stimulation. A schematic system block diagram 1000 is shown for a single channel for illustrative purposes in FIG. 10. The controller may house the electronics for each of the channels including the control processor 1002, which may interface with a host computer 1001 (or other device). New stimulation waveforms, log files, system control and setup, etc. may be input or otherwise performed by the computer 1001 which interfaces with the control processor 1002.

For each channel, the control processor 1002 may send the data to a digital-to-analog converter (DAC) 1003 to control the output from the voltage source 1004 to the corresponding electrode pair 1005 when positioned into proximity with the target. A potentiometer or variable resistor 1006 may be electrically coupled with a voltage amplifier 1007 which in turn is electrically coupled to the processor 1002 via an analog-to-digital converter (ADC) 1008 to provide feedback to the processor 1002. An open circuit detection circuit may be in communication with the processor 1002 from the electrode pair 1005 and via a voltage amplifier 1009 and an analog-to-digital converter (ADC) 1010, as shown, for determining whether an open circuit is present. The current read by the ADC across each electrode may be, e.g., 1 mA, while the voltage across each electrode may be, e.g., 10 V. The impedance value across each electrode may be calculated by the RMS of resistances over a 1 second interval:

$$V_{rms} = \sqrt{\frac{\sum_{n=1}^{w} (V_n)^2}{w}} \quad (1)$$

where w equals the 1 second window.

The controller may output a maximum of, e.g., 80V (+/−40V), which may be adjusted by the software to maintain a current over an electrode-to-scalp connection impedance range from, e.g., 4 to 40,000 Ohms. For this reason, a current source is desirable where a frequency range for DC may range up to 10 kHz. The impedance of the system may be monitored and checked automatically by the controller, e.g., once per minute, and the mean impedance may be calculated across the entire electrode array. Additionally, the impedance values may be monitored and measured for each channel independently of one another. Because of the possible hardware and software combination, the current and voltage specifications on individual channels do not need to sum to zero thus allowing current steering across a plurality of channels where the total current sums to zero.

With the electrodes desirably positioned upon the patient's head, the electrical stimulation may be applied in a ramped manner so that the current is not applied instantly but is applied at an increasing level over a specified period of time. In the event that the impedance is detected to exceed 40,000 Ohm, the controller 501 may be programmed to automatically ramp down the stimulation over a specified period of time, e.g., 10 secs. An alert or alarm may be activated and the device may be placed into a pause mode. Once treatment has been completed, the current may also be reduced at a decreasing level over a specified period of time. Ramping up and ramping down the current may help to avoid any damage to the patient's brain.

The electrode housing 701 may optionally incorporate one or more sensors and/or the controller 501 may be programmed to monitor the impedance after the electrode housing 701 has been applied to the patient's scalp. Before, during, and/or after treatment, the impedance may be monitored to detect for changes in the impedance value. For instance, if a high impedance is detected, the controller 501 may be programmed to provide an alert or alarm to the user or practitioner and the device may be automatically terminated. Furthermore, the current output may be maintained via a hardware control loop and also monitored via a software control loop.

Figure 11:
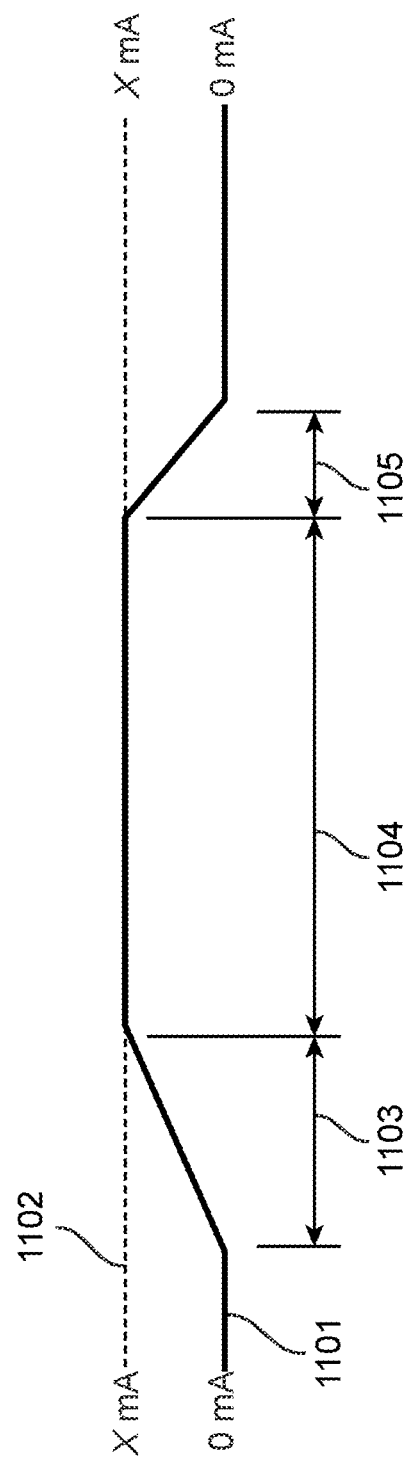
FIG. 11 shows a graph illustrating one example for applying the stimulation to the patient.

FIG. 11 shows a graph illustrating one example for applying the electrical stimulation to the patient where the initial current 1101, e.g., 0 mA, may be increased over a ramp up period 1103 until the treatment level 1102 (e.g., X mA) has been reached with an output constant current maximum of, e.g., 4 mA peak magnitude. The applied electrical stimulation may be applied so that the treatment level 1102 is reached over a predetermined period of time during the ramp up period 1103 so as to avoid any potential injury to the patient's tissue. For instance, the applied current may be increased over a period of, e.g., 10 secs to 15 mins, during the ramp up period 1103 where the current may be increased at intervals of, e.g., 1 sec. An example may include ramping the current up and/or down each over a 15 sec period although the ramp up and/or ramp down period may be adjustable.

The electrical stimulation parameters may be controlled by the controller 501 and the stimulation may be applied in a number of different modalities. For instance, the applied stimulation may be time varying in the form of sinusoidal waves having a frequency of, e.g., 0 to 10,000 Hz. Additionally, the stimulation may be adapted and arranged to allow for the combination of sinusoidal waves to produce complex, time-varying waveforms that may mimic the activity and variability of a working brain.

The electrical stimulation may be applied at the treatment level 1102 for a specified period of time over the treatment period 1104 which may range anywhere from, e.g., 0.1 mins to 60 mins, in 0.1 min increments. The treatment level 1102 may also range anywhere from, e.g., 0.1 mA to 4 mA, where the treatment level may be varied in, e.g., 0.1 mA increments. At the higher end of voltage, the current may be ramped downwards to, e.g., 2 mA. The length and intensity of the treatment may be controlled through the controller, e.g., controller 501. The practitioner may program the controller with the various treatment parameters or they may be pre-set or controllable in real time via a remotely located controller. In the event that the controller 501 is controlled remotely, communication to the controller 501 may be maintained through various wireless or wired modalities.

The controller 501 may optionally include a user interface which allows for the practitioner and/or patient to interface with the controller 501 to enable the entry and/or display of various treatment parameters or the interface may simply comprise simplified external controls, e.g., controls which turn the treatment device on/off or pauses the treatment.

The controller may also be configured to wirelessly transmit data to and/or receive data from a device which is located remotely from the controller. Hence, the controller may transmit data sensed from the electrodes as well as receive data from the remote device, e.g., computer, laptop, tablet, smartphone, etc., such as treatment parameters, power levels, stimulation waveforms, etc. Moreover, this communication may occur through various wireless protocols, e.g., internet, cellular, RF, etc. As the controller may be configured with a network interface, this interface may be configured to remotely receive servicing or activation signals in response to brain or behavior states. All wired inputs to the controller including the charger, trigger, and network lines will be optically isolated to protect the person receiving the stimulation from voltages transferred from the wall socket.

In the event the treatment system incorporates a pause mode to allow the practitioner or user to temporarily pause a treatment session, stimulation may be resumed after the pause. The system may be configured to wait for a predetermined period of time following the initiation of the pause mode after which treatment resumes automatically or the treatment may be resumed after being affirmatively re-started by the practitioner.

After the treatment period 1104, the stimulation may be reduced over a ramp down period 1105 until the initial current level 1001 has been reached or until the system has shut off. Like the ramp up period 1103, the stimulation may be reduced over the ramp down period 1105 which may range anywhere from, e.g., 10 secs to 15 mins, during which the current may be decreased at intervals of, e.g., 1 sec. The controller 501 may be optionally programmed to prevent the sudden starting or stopping of a treatment as a safety measure and to also ensure that the ramp up period 1103 and ramp down period 1105 are sufficiently timed and stepped in intensity.

The controller 501 may be optionally further programmed to time-out or lock-out any further treatment once a treatment session has been completed for a specified period of time, e.g., 2 hrs to 36 hrs or more. This feature can be adapted and arranged as a safety feature in a number of different ways to limit use of the device to safe treatment intervals.

Additionally and/or optionally, the controller 501 may be further programmed to reverse the polarity of the electrodes 703 when placed in the electrode housing 701 following a treatment session as maintenance to prevent corrosion of the connections of the individual electrodes and preserve the useful life of the electrodes 703.

Treatment (Neuroimaging-Guided Noninvasive Brain Stimulation)

Generally, application of the electrical stimulation for treatment of subjects or patients may involve the steps of (1) recording the subject's brain activity at different states, (2) evaluating the differences between the different recorded states, (3) finite element modeling of the current paths in the brain to target brain state unique activations identified in the difference images from neuroimaging, and then (4) stimulating the subject's brain according to the modeled image; otherwise known as a ng-NIBS technique.

In determining the location for placing the electrode array upon the patient's head, c-TDCS generally involves utilizing only a general knowledge about the brain, the brain's cognitive functions, and the task at hand to target brain stimulation and is thus sub-optimal in locating and treating specific regions of the brain. Hence, all the challenges associated with c-TDCS may be overcome by utilizing neuroimaging-guided TDCS (ng-TDCS) which assumes no prior knowledge of the different brain areas, cognitive processes and the task at hand. Moreover, ng-TDCS empirically determines the brain areas that are involved in the performance of the task by measuring task-related brain activity with one or more neuroimaging modalities, e.g., magnetoencephalography (MEG), electroencephalography (EEG), functional magnetic resonance imaging (fMRI), positron emission tomography (PET), single photon emission computed tomography (SPECT), electrocorticography (ECOG), structural magnetic resonance imaging (sMRI), diffusion tensor imaging (OTT), magnetic resonance spectroscopy (MRS), functional near infrared spectroscopy (fNIRS), etc.

The brain activity is localized to the particular brain structure(s) that are activated in low performance states (e.g., novices) and high performance states (e.g. experts). The images of the brain activity in the low performance states and high performance states are then coregistered and subtracted to produce a difference image that contains only the areas of brain activity that change between low performance and high performance states.

The ng-TDCS (and related electrical, magnetic, optical, and ultrasonic NIBS methods) technique takes advantage of the fact that there are desirable brain states that lead to behaviors that are well suited to the tasks and undesirable brain states that lead to poor performance on the same tasks. Desired brain states that aide performance could be attentive, happy, expert, quick while comparable undesirable brain states might be inattentive, sad, untrained, or slow, injured. ng-TDCS uses data from, e.g., MEG, EEG, fMRI, PET, SPECT, ECOG, fNIRS, sMRI, DTI, MRS, and other technologies to record data in the desirable and undesirable brain states, and in one embodiment, maps the recorded brain activity to the structures of origin in the brain using commonly available algorithms.

The mapping to brain structures is done twice, once for desirable and again for undesirable brain states. This provides the basis for comparing and contrasting the structural and functional brain states that contribute to the difference between performance with desirable and undesirable outcomes. Thereby, determining the target brain region(s) where the influence of electrical NIBS could move the user from an undesired to a desired brain state. The ng-NIBS approach differs from the standard practice of electrical NIBS where neuroimaging is rarely used determine target brain structures. When no neuroimaging is performed the user must rely on often poorly founded assumptions about both the current paths in electrical NIBS and task-related brain activity.

This difference image is fed into a finite element model that can be used to accurately calculate the path of electrical currents through the head as they pass between electrical NIBS electrodes where at least one is placed on the scalp. The electrodes described herein may be placed at locations on the scalp that pass maximal current density through target brain tissues that differentiate brain state and task related brain activity. A single electrode polarity may be placed on the scalp at this location, e.g., either anode to enhance brain activity or cathode to suppress brain activity. The other electrode may be placed on another portion of the subject's body, e.g., the upper arm, to eliminate problems caused by the placement of both anode and cathode on the scalp. This aspect straightforwardly enhances or suppresses brain activity without any complicating effects of both electrodes on the scalp. Utilizing this ng-TDCS treatment can increase learning performance by 100% rather than the 10%-20% commonly observed in c-TDCS experiments.

For evaluating the differences between brain states, the ng-NIBS technique calculates the target for electrical NIBS by comparing and contrasting MEG, EEG. fMRI, PET, SPECT, ECOG, fNRS, sMRI, DT1, MRS, and other techniques from two different brain states. In one embodiment, the calculation could be made across individuals where a group of individuals with a desired brain state is compared to a group of individuals with an undesirable brain state; inattentive individuals could be compared to those who are attentive, expert individuals could be compared to novices, depressed individuals could be compared to healthy subjects, brain injured individuals could be compared to healthy individuals, individuals that perform a cognitive operation quickly could be compared to those who work more slowly. This is a "one size fits most" approach to the problem of optimizing ng-NIBS.

In another embodiment, neuroimaging methods compare brain states within individuals across time, i.e. the brain states associated with correct responses could be compared to those recorded during incorrect responses, attentive could be compared to inattentive, novice could be compared to expert, tired could be compared to wide awake. The comparison of desirable and undesirable brain state within an individual could be used to develop customized electrode arrangements for ng-NIBS in each individual.

In yet another aspect, the present technology can employ various kinds of comparisons of various kinds of brain activities with respect to the same brain in order to determine the most advantageous locations or conformations of electrodes. Thus, the analyses of one or more brain activities that are used to determine the correctly positioned or conformed electrodes and arrays of electrodes for delivering electrical NIBS can include many different parameters. Such parameters include, but are not limited to, the location, amplitude, timing, phase, frequency, and duration of one or more activities in one or more brain areas. The recorded brain activity thus obtained is especially useful when the data recorded gives information about the consistency or causation of amplitude relationships, time relationships, phase relationships, frequency relationships, and the duration relationships across multiple similar events processed by the brain, or across regions in the brain. However, the application of this method to determine the optimal brain targets for electrical NIBS is both innovative and extremely useful. The ng-NIBS approach allows both functional (e.g., MEG, EEG, fMRI, tNIRS, PET, SPECT, ECOG, and MRS) and structural (e.g., sMRI, DTI) comparisons between and within subjects. Previous studies have shown that one type of electrical NIBS, TDCS, can alter measures of DTI that indicate the white matter tracts in the brain have decreased radial diffusivity in the hemisphere ipsilateral to stimulation.

This is typically interpreted as increased myelination and/or healthier white matter. This raises many possibilities for the uses of electrical NIBS in rehabilitation and white matter diseases of the brain that occur with aging, Virchow-Robin Perivascular Spaces, deep white matter ischemia, multiple sclerosis, progressive multifocal leukoencephalopathy, post-infections encephalitis, HIV related encephalitis, radiation injury, chemotherapy neurotoxicity (chemobrain), posterior reversible encephalopathy syndrome, central pontine myelinolysis, the leukodystrophies and the adreno leukodystrophies, as well as peripheral and central nervous system damage from traumatic brain injury, concussion, chronic traumatic encephalopathy, spinal cord injury, and stroke. All of these diseases could be treated with the embodiments that do comparisons across or within individuals to identify targets for electrical NIBS in the CNS. The idea of comparing and contrasting brain activity in two conditions or across two populations is not novel. However, evaluating the differences in advanced neuroimaging techniques between populations in order to guide electrical NIBS is quite novel. This approach has been used successfully to double the rate of learning in multiple laboratories and on multiple tasks. This allows for evaluation of the differences between desired and undesired brain states.

Furthermore, the ng-TDCS is a method that could be expanded to include different types of brain stimulation. For instance, ng-TDCS becomes neuroimaging-guided non-invasive brain stimulation (ng-NIBS) and the principles of ng-NIBS could be expanded to include, e.g., transcranial magnetic stimulation (TMS), repetitive TMS (rTMS), pulsed electromagnetic fields (PEMF), transcranial alternating current stimulation (TACS), transcranial random noise stimulation (TRNS), time varying electrical stimulation (TVES), ultrasound brain stimulation (UBS), etc. Moreover, the various hardware and software combinations may allow for the channels to operate with independent or common references to create TDCS, TACS, TRNS, and TVES presentable in any combination across single or multiple channels.

In recording the brain activity of a subject's brain, the step or action of (1) recording brain activity (data) may be accomplished by any one or more imaging modalities, as described herein, during desirable and non-desirable brain states. Examples of desirable brain states which are useful for practicing the present methods include: attentive, expert, healthy, uninjured, cognitively fast, and cognitively flexible. Examples of undesirable brain states include: inattentive, untrained, depressed, brain injured (such as TBI), cognitively slow, cognitively rigid.

In another aspect, one embodiment of a method of the invention includes the step or action of (2) evaluating the differences in the subject brain or brains between desirable and non-desirable brain states. This difference evaluation is performed with respect to the brain activity data obtained by one or more of the initial steps or actions of this embodiment of the method of the invention. The results of this difference evaluation between desirable and non-desirable brain states can then be used to determine portions, regions or parts of the subject brain or brains which are suitable targets for electrical NIBS. By effecting NIBS of these target parts of the subject brain or brains, brain circuitry can influenced to transition from an undesirable to a desirable state. The advantages of this transition can be numerous.

In yet another aspect, the data obtained in the present method can be used to (3) virtualize the differences between the desirable and non-desirable brain states to effect a determination of one or more advantageous electrode array designs and configurations which are suitable for specific desired purposes, such as the teaching of languages, the enhancing of decision making, the increasing of vigilance, the increasing of cognitive flexibility, the enhancing of creativity, the teaching of the correct accents for languages, the increasing of attention, the enhancing of sleep. the reversing of brain damage (such as that associated with traumatic brain injury, stroke, concussion, hypoxia, and chemical or other injury), and the treating of symptoms of mental illness (i.e. reducing hallucinations, elevating mood, alleviating flattened affect, reducing anxiety, reducing insomnia, reducing unwanted memory, enhancing social skills, reducing repetitive thoughts, reducing social phobias).

With the present technology, electrodes and electrode arrays can be designed and configurations of arrays as described herein, including how the electrodes communicate with one another and with other components of the invention, can be effected to maximize the effectiveness of NIBS-based neurological interventions. Such designs and configurations can be effected with respect to, among other factors, spatial positions of the electrodes in two or more dimensions, the respective polarities of the electrodes, the timing of activity on or between electrodes, the frequency (typically in terms of Hz) delivered by one or more electrodes, the frequency of stimulation in terms of repetition of a determined stimulation regimen, the latency of the stimulation, if any, on an electrode or electrodes with respect to environmental events, the correlation among stimulation parameters across electrodes, the correlation of stimulation with environmental events, the phase relationships among stimulation parameters across electrodes, the duration of stimulation on an electrode or electrodes and the relationships of these durations across electrodes, causal inferences from recordings of activity that are replayed to the brain via an electrode or electrodes, and the intensity or intensities of the electrical stimulation delivered by the respective electrodes, such that the NIBS stimulations can have the greatest desirable influence on targeted brain areas.

Figure 12A:
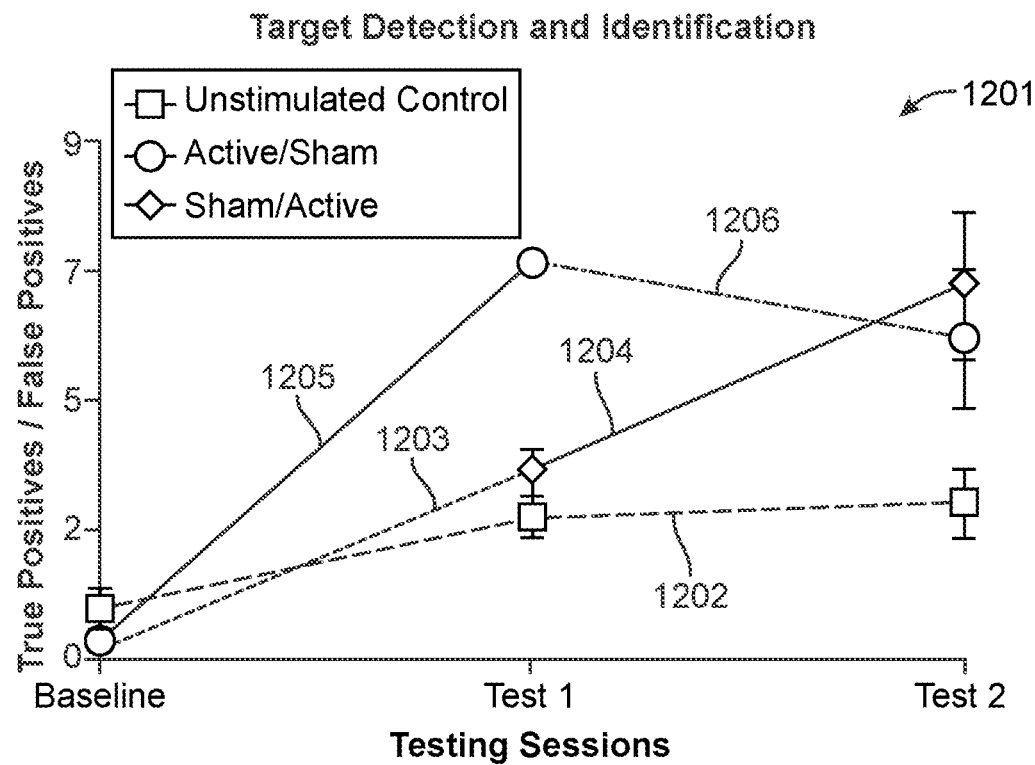
FIG. 12A shows a graph illustrating the differences in target detection and identification between treatment sessions when applying active electrical stimulation and sham stimulation.

With respect to the effects of the ng-TDCS stimulation treatment, FIG. 12A illustrates graph 1201 which shows experimental sample results of subjects who have performed a target detection and identification task before and during the application of electrical stimulation with ng-TDCS. The task results from an un-stimulated control group 1202 is shown at a baseline, after a first test (Test 1), and after a second test (Test 2), where stimulation was not applied at all. A second group was tested at the baseline, after Test 1 where no stimulation was applied 1203 (i.e., sham), and after Test 2 where stimulation was applied 1204. The number of True Positives/False Positives increased accordingly from the no stimulation 1203 to when stimulation was applied 1204. Likewise, a third group was tested at the baseline, after Test 1 where stimulation was applied 1205, and after Test 2 where no stimulation was applied 1206. Accordingly, the number of True Positives/False Positives decreased from when the stimulation was applied 1205 to when no stimulation was applied 1206.

Figure 12B:
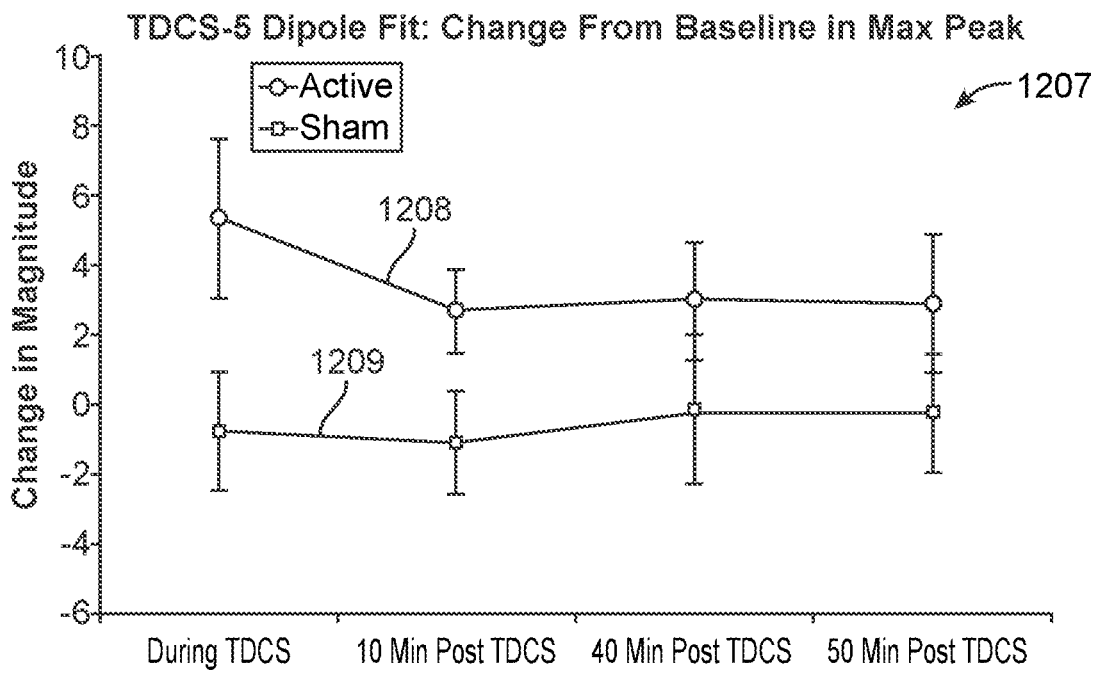
FIG. 12B shows a graph illustrating the difference between active electrical stimulation and sham stimulation over time.

Furthermore, additional experiments of subjects have shown that the effect of ng-TDCS stimulation has lasting residual effects after the treatment has ended. For instance, FIG. 12B shows a graph 1207 which tracked the results of enhanced brain function between a first group of subjects 1208 during ng-TDCS stimulation, 10 min. post TDCS stimulation, 40 min. post TDCS stimulation, and 50 min. post TDCS stimulation. This is compared to a second group of subjects 1209 which had a sham treatment applied and who were tested over the same time periods. Accordingly, the first group 1208 showed a significant change in magnitude over the second group 1209 who had a sham treatment applied for a period of time even after the stimulation has ended.

Figure 13A:
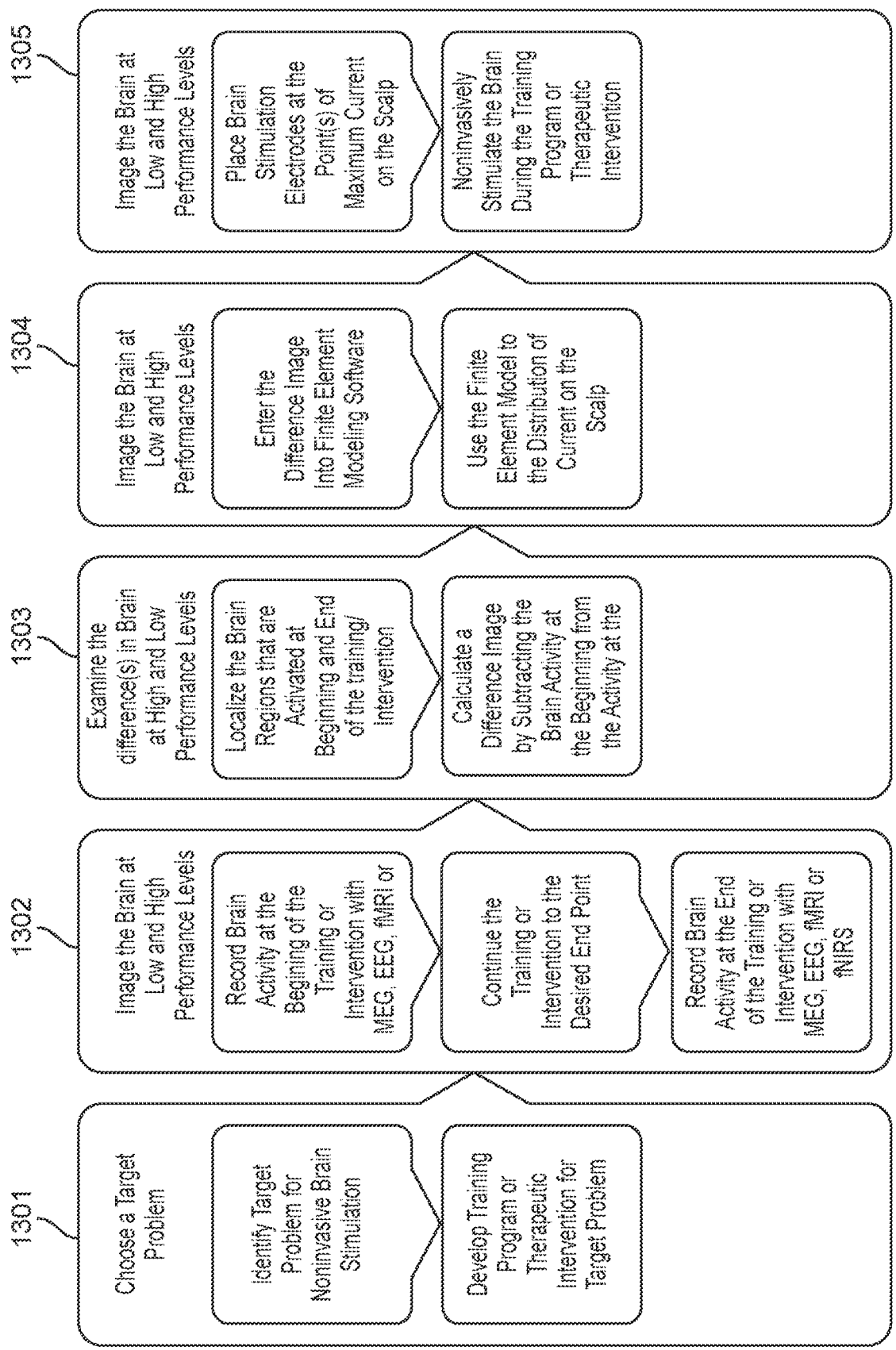
FIG. 13A shows a flow chart of one method for utilizing neuroimaging-guided non-invasive brain stimulation.

FIG. 13A illustrates a flow chart showing the various steps in further detail for applying a ng-TDCS treatment. Initially, a target problem may be chosen 1301 which may involve identifying a target problem for noninvasive brain stimulation and then developing a training program or therapeutic intervention for the identified target problem. The brain may then be imaged at both the low performance level and the high performance level 1302. This step may include recording the brain activity at the beginning of the training or intervention using any number of various neuroimaging modalities. The training or intervention may be continued to a desired end point and the brain activity may be recorded at the end of the training or intervention period again using any number of various neuroimaging modalities.

Once the brain has been imaged, the differences in the brain activity at the high and low performance levels 1303 may be examined. This includes localizing the brain regions that are activated at the beginning and end of the training or intervention and then calculating a difference image by subtracting the brain activity at the beginning from the activity at the end. The difference image may be entered into finite element modeling (FEM) software 1304 (e.g., SIMULIA, Dassault Systemes or other similar FEM software) which may be used to model the distribution of current from electrical NIBS in the brain of the subject. With the known current distribution, the electrodes may be positioned on the scalp at locations that pass the maximum current through target structures 1305 using electrical ng-NIBS during, e.g., a training program or therapeutic intervention.

According to some preferred specific embodiments of the present technology, an EEG, fMRI or MEG device is used to measure the location, amplitude, and magnitude of time dependent electric and/or magnetic field oscillations that are recorded as one or more outputs or response from the brain in various circumstances. These oscillations that indicate neural activity can be related to normal functions such as the sleep cycle, pattern recognition, learning, teaching, various types of communications and decision making. These signals can also be indicative of abnormal functions caused by sleep deprivation, stress, epilepsy, autism, addiction, and stress disorders.

In another key aspect, users of the present methods, devices and arrays can determine the influence of electrical NIBS to a brain or a group of brains. By way of example, after a target for electrical NIBS is determined in the Recording and Evaluation phases of ng-NIBS, the amplitude, polarity, and spatial location of the electrodes that have the greatest influence on the brain structure(s). This is accomplished with finite element modeling. In one aspect, finite element modeling divides the brain, scalp, skull, and surrounding tissues into different layers that can be used to make predictions about the path that electrical NIBS will take through the tissues that surround the brain to get to targeted brain structures. The finite element models are generated from high resolution sMRI. The different gray levels in sMRI images are due to different concentrations of water in the tissues. The different gray levels allow the tissues to be segmented into separate layers and tissue compartments. The layers and tissue compartments are then tessellated across the surface with triangular meshes.

The tessellated meshes can then be assigned a value for how well electricity is conducted through the volume of tissue. Collectively, the layers and tissue volumes in the finite element model are called the forward model. In ng-NIBS the area(s) of the brain identified as targets for stimulation to enhance desirable brain states will be virtually activated in the finite element model. The virtual activation of the brain area will project electricity through the forward model and onto the scalp surface. The identified areas of the cortical surface will be the locations for the spatial position of the electrodes. The polarity of the currents that are shown on the scalp will determine the polarity of the currents that are delivered at each spatial position. The strength of the current that is projected onto the scalp surface will determine the proposition of the total current that is delivered at each electrode position.

While the finite element model is used to target the brain structures, it is not used to target the regions of maximum current on the scalp. Rather, the electrodes may be moved around the scalp until the current passing through the target brain structure is maximized. That is, FEM is used to determine where the underlying current is passing through the brain structure and FEM helps to iterate which brain regions are affected for targeting and determining the ultimate electrode positioning relative to the scalp.

Another aspect is that the present methods can be used to target either gray matter (the parts of the brain containing the parts of the neurons that perform the computations necessary for sensation, perception, cognition, emotion, movement, thought, and other behaviors) or the white matter (the connecting tissue between specialized parts of the brain that work together to produce sensation, perception, cognition, emotion, movement, thought, and other behaviors).

Figure 13B:
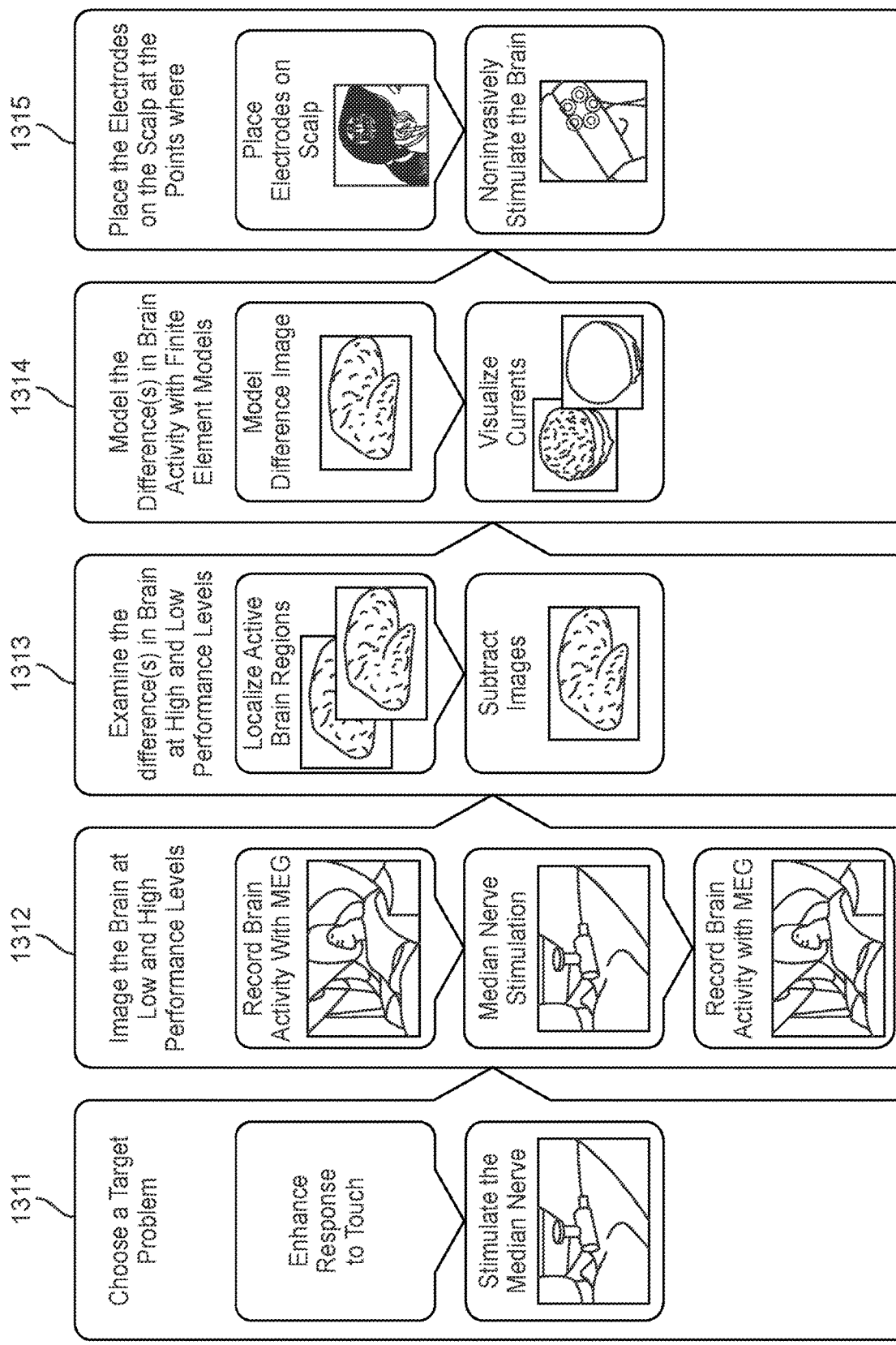
FIG. 13B shows a flow chart illustrating specific examples for utilizing neuroimaging-guided non-invasive brain stimulation.

FIG. 13B illustrates a flow chart with examples of the various steps in further detail for applying an ng-TDCS treatment. In choosing a target problem 1311, one example illustrates how enhancing a subject's response to touch may be approached by, e.g., stimulating the subject's median nerve in combination with ng-NIBS. The subject's brain may be imaged at both the low performance level and the high performance level 1312 by first recording the subjects brain activity with any of the neuroimaging modalities, then stimulating the median nerve with pulses at the wrist that are below threshold for producing sensation and then recording the subject's brain activity again with stronger pulses that are suprathreshold.

The differences in the subject's brain at both the sub- and suprathreshold performance levels may then be examined 1313 where the difference image may be calculated by subtracting the localized active brain regions between the high and low sensation levels, as illustrated by the difference images at the respective median nerve stimulation levels.

This resulting difference image may be entered into FEM software 1314 which may then be used to model the distribution of current in the subject's brain as a result of electrical NIBS, as illustrated. With the known current distribution, the electrodes may be adjusted in position relative to the scalp 1315 until the current passing through the targeted brain structure is maximized and the subject's brain may then be non-invasively stimulated in a targeted manner using any of the methods and devices described herein.

Stimulation of one or a plurality of brains with electrical NIBS provides manifold advantages and uses. In yet an additional aspect of the present technology, the pattern(s) of stimulation that can be designed to stimulate brain regions that will increase the likelihood of a desired brain state from the recording and localizing of brain activity, creation of the difference image, and use of the finite element modeling (FEM) portions of ng-NIBS can be programmed into a device of the invention as described herein. Such programming will typically utilize 5 to 10 electrodes on the scalp surface and up to 5 extracephalic electrodes, although any number of electrodes can be adapted to the present devices and methods. The lengths of the up to 10 curved plastic arms that hold the electrodes will be tailored to the position on the scalp that is necessary to target the ng-NIBS determined brain structure. The angle at which each aim need to leave the head frame will be set by a mechanism of grooves that locks the arms into the appropriate angle. The polarity and amplitude of electrical NIBS will be set to mimic the pattern observed in the finite element model.

The tailoring of the arm length and the setting of amplitudes and magnitudes can be determined from data collected across individuals or within an individual and for targeting structure or functional differences between desired and undesired brain states. The electrical NIBS device is now programmed to facilitate a one specific desirable brain state or structure. The device would need to be reprogrammed and newly tailored for producing a different desirable brain state. The list of desirable brain states is very large but several specific examples will be given below.

Another useful and innovative with respect to the present technology comprises one or more methods for determining the appropriate target for electrical NIBS in the brain. At present, conventional methods for determining the brain region(s) to be targeted with electrical NIBS are largely based on textbook descriptions of cognitive functions and/or work that details functions that are lost after strokes or brain lesions. Determining target brain tissues with this "lesions and literature" methodology makes multiple fallacious assumptions. These include: 1) all brains are the same, 2) loss of function with lesion indicates the location of function, 3) the area of brain directly underneath the electrode is most effected by the electrical NIBS, and 4) laboratory tasks are good proxies for the activities of daily Life in terms of brain activation and prediction of success. The methods disclosed herein in one or more embodiments can be individualized, and customized or matched to appropriate patterns of brain activity, and deployed into daily life to enhance desirable behaviors and reduce undesirable behaviors by electrical NIBS that enhances or reduces activity in appropriate brain regions.

In another embodiment it can be configured in a "one size fits most" configuration that is not designed to be individualized. In both embodiments, the method requires recording brain activity during desirable and undesirable conditions or responses. The patterns of brain activity or structure in the desirable and undesirable conditions are then compared to glean the location and direction in which brain activity or structure must be changed to move from an undesirable to a desirable state of performance. In one embodiment, the effects of electrical NIBS on the brain can then be determined with finite element models that use electrodes in various spatial configurations, strengths, and polarities to determine the most favorable arrangement of a plurality of electrodes that will maximally effect the brain region(s) that is being targeted to alter behavior or deliver therapeutic intervention through excitation or inhibition or structural change.

The optimal spatial configuration, strength, and polarity can then be implemented on the device described above to apply stimulation to the brain to enhance performance or provide therapy through brain excitation, inhibition or structural change. ng-NIBS is distinct from the lesions and literature approach in multiple ways. 1) There are no a priori assumptions made about the location(s), strength(s), or temporal characteristics of brain activity or structure. 2) ng-NIBS uses brain states associated with different behavioral patterns in an individual or group of individuals to determine the appropriate brain areas for targeted stimulation. 3) ng-NIBS makes no apriori assumptions about how the effects of electrical NI BS are distributed in the brain; it models them virtually. 4) ng-NIBS is readily amenable to individualization (ing-NIBS) to not only to specific persons but also to specific brain states within a person as they vary across the day when the embodiment records activity and delivers stimulation as part of a single device.

In one aspect, the time dependent electric field oscillations provide the measurements to one or more devices or networks of the invention, which are able to interpret the measurements, identify signals that are indicative of an abnormal or undesirable function, and generate a modified signal that can be transmitted into the brain using a transcranial brain stimulator such as transcranial Direct Current Stimulation (tDCS), transcranial alternating current stimulation (tACS) or Transcranial Magnetic Stimulation (TMS) in order to produce a desired effect. As one example of one specific embodiment of the numerous embodiments of the present invention, if the detected brain output is indicative of the onset of an undesirable brain process, such as the initial stage of a seizure, then the signal generated by the device and delivered to the brain would provide an in-phase, equal magnitude, but opposite sign in order to cancel that signal through destructive interference with the output signal. This superposition of an opposite sign (or cancelling) signal is similar in some aspects to known methods of acoustic noise cancellation commonly used in active acoustic noise cancellation headphones and speakers. Accordingly, a unique feature of the inventions provided in this disclosure is the application of one or more "cancellation signals" within the brain region generating the undesirable output signal.

The application of a pulsed, oscillating, or DC electric field to modify neural activity is known in the art. These approaches typically apply a stimulus in an on/off manner based on a prescribed dose/time relationship. In stark contrast, according to various embodiments, the presently described invention may utilize closed loop feedback in order to provide active modification of a device-generated input signal in response to the brain's output signal.

According to another embodiment of the invention, a feedback device is connected to electrodes that are place on the head in locations that are optimized for activation or deactivation of signals of interest that are produced by the brain. For instance, if the output is indicative of the early stage of a seizure in a localized brain region, the electrodes are located to provide or direct a cancellation wave to the part of the brain responsible for generating the early stage seizure related signals in order to prevent the growth of wide spread coupled brain oscillations. According to various embodiment s, at least a portion of the feedback device could take the form of a headset, cap, hat, helmet, head draping, headband or pillow. For instance, the headgear 802 shown above in FIG. 8 may incorporate such a feedback device.

According to yet another embodiment, the feedback device could be placed and optimized to encourage the brain to generate particular signals, or cycles of particular signals, that are adapted and arranged to fulfill one or more desired functions. For example, a suitable application envisaged by the inventor is to treat sleep deprivation caused by undesirable rapid transition from non-REM sleep into REM sleep. In this one of many embodiments, the purpose of the input field would be to entrain the signals produced by the brain that are associated with healthy sleep cycles and reduce the frequency of maladaptive patterns of sleep. In one alternative, the feedback device could be designed to encourage restorative slow wave sleep and prevent quick or premature transition into REM sleep. Control of sleep brain patterns, either by preventing undesirable signals or by controlling the signal patterns over time could help reduce or prevent nightmares, and/or produce sleep that is more restorative over shorter durations, essentially allowing for an electrically stimulated powernap. Similar patterns could be profoundly useful for treatment of disorders such as post-traumatic stress disorder (PTSD).

Alternatively stated, the feedback device could be designed such that one or more electrodes are placed so as to direct the feedback device-generated signal towards those regions of the brain (the target regions. portions or structures) that are responsible for generating the signal of interest. In some embodiments, arrays of electrodes may be utilized to localize or concentrate feedback device-generated signals to one or more specific regions (the target regions, portions or structures) of the brain.

According to still another embodiment, the feedback device could be placed and optimized not to cancel an undesirable signal, but rather to amplify a desirable, naturally occurring signal. In yet another alternative of some of the key present methods, the feedback device could cancel or suppress some signals of interest, while amplifying others. For example, in applications (methods) to enhance memory, learning, or pattern recognition, the detection of a desirable signal would allow the feedback device to amplify that signal associated with storage of the information of interest separately, or in concert, with suppressing cognitive processes that compete for resources that could be used to encode memory.

For example, in one embodiment adapted for the purpose of teaching one or more languages, the brain activity and structure of one or more subject groups are recorded with one or more neuroimaging methods with respect to both desirable and undesirable brain states defined as fluent and non-fluent, respectively, according to the present methods. The differences between the desirable and undesirable states are then evaluated in order to produce an electrode array that will facilitate language learning in many individuals.

As an aspect of teaching languages, individual enhancement strategies can be tailored, developed or customized to one or a group of people. As an example of certain parameters of methods of the invention, the brain activity and structure-of a single subject can be recorded in desirable and undesirable brain states. The data thereby obtained can be used, for example, to determine and teach such nuances of language learning such as inflection, accent and rhythm. The difference between such desirable and undesirable brain states can advantageously be evaluated to produce an electrode array that is customized to enhance performance in a particular individual and may or may not be applicable to other individuals.

Similar strategies can be applied to many different types of learning dynamics. Thus, general aspects of the present methods can be applied to thereby achieve numerous different learning scenarios. As additional examples, the present methods, techniques and procedures, with the benefit of the present specification, can be directed toward the reduction of fatigue, of either an individual or a group.

According to yet another embodiment, two or more feedback device could be in electrical communication with one another. In such embodiments, a feedback device of a first individual could transmit information to the feedback device of another individual or to the feedback devices of a group of individuals in order to enhance team performance by manipulating attention, engagement, and/or coordination of the group.

In one of many possible military applications involved in a small group attempting to deal with ambiguous unstructured information, the coupling of multiple feedback devices would lead to enhanced detection of relevant information and coordination of the group. For example, if the feedback device of one member of a group identified brain waves associated with increased alertness, for example in response to the individual noticing "unusual or suspicious activity," the feedback devices of the other members of the group could be programmed to increase alertness for all members of the group within a predetermined proximity, or those who are chosen to be in a particular communications network.

According to another embodiment, the individual feedback device could be coupled to remotely located computers to provide additional real time processing and memory for each of the feedback devices. These computers could then be connected into a feedback and control system to provide overall management and coordination of the ensemble. For example, the feedback devices could be used to enhance the performance of a team of cyber defenders who are dealing with rapidly changing ambiguous information. The ability to detect pre-conscious patterns is known in the art, and the sharing of these preconscious detections would enhance the speed and coordination of the group. The ability to amplify this detection capability of the individuals and the group would lead to substantial performance enhancements of both the individuals, and of the group as a whole. According to yet another embodiment, rather than generating a signal that is equal and opposite to the signal of interest, the feedback device could introduce white noise so as to disrupt the signal of interest.

In accordance with the several objects of the invention, a variably configurable electrode array is provided, wherein the array comprises: at least two electrodes, wherein each of the electrodes is operationally connected to the other electrodes, or to at least one microprocessor; a housing adapted and arranged for variably positioning the electrodes with respect to one another, and for variably positioning each of the electrodes respectively in operational proximity to one or more regions, areas or points of a scalp of a subject upon which the array is placed; at least one microprocessor located in operational proximity to the housing, wherein the microprocessor is adapted and arranged to process data collected by means of the electrodes; and at least one data storage module located in operational proximity to the array, wherein the module is adapted and arranged to be operationally connectable to one or more of the at least two electrodes and the at least one microprocessor; and software suitable for storing software, wherein the software is adapted and arranged for one or more of operating one or more functions of the array, storing data collected by the array and processing data. Preferably, an array of the invention further comprises a battery or other means adapted and arranged for providing electrical power to the array or to objects or modules attached to the array.

In one aspect, the present technology can employ various kinds of comparisons of various kinds of brain activities with respect to the same brain in order to determine the most advantageous locations or conformations of electrodes. Thus, the analyses of one or more brain activities that are used to determine the correctly positioned or conformed electrodes and arrays of electrodes for delivering electrical NIBS can include many different parameters. Such parameters included, but are not limited to, the location, amplitude, timing, phase, frequency, and duration of one or more activities in one or more brain areas. The recorded brain activity thus obtained is especially useful when the data recorded gives information about the consistency or causation of amplitude relationships, time relationships phase relationships, frequency relationships, and the duration relationships across multiple similar events processed by the brain, or across regions in the brain.

In yet another series of embodiments of the invention, one or more kits are provided. In some embodiments, a kit of the invention may comprise at least one array, software necessary to operate the array in all desired aspects, and task software contained in operational connection or within the array housing directed toward one or more specific purposes. Task software in this context can be any software adapted and arranged for facilitating any task for which the kit is directed. Task software for use with the invention is preferably one or more from the group comprising language learning software, ability testing software, diagnostic software, and intervention software.

In yet another set of embodiments, the present invention includes one or more networks, wherein each network comprises a plurality of variably configurable electrode arrays, and wherein the plurality of arrays are adapted and arranged to be in operative communication with another while one or a plurality of the arrays are in operational proximity to one or a plurality of the scalps of one or more subjects. A network of the invention may further comprise a control module, wherein the control module is adapted and arranged for facilitating a plurality of control functions of the arrays and of the network. Preferable control functions of the network include, as examples, one or more of oscillations of a particular frequency, time varying functions on a single electrode and coordinated with time varying functions on a plurality of electrodes that can vary with respect to correlation, causality, duration, phase, latency, amplitude, and frequency. Moreover, multiple units may allow for separate units to be stackable such that the number of stimulation channels can be increased to multiples of the channel number in each stimulator and made to work in combination when the devices are either collocated or remote from one another.

In some embodiments of the invention, one or more of the microprocessor, the software, and the data storage module are one or more of i) in operative communication with one another, ii) in operative communication with one or more networks, and iii) in operative communication with humans or computer systems external to the array. In a somewhat similar context, or more of the microprocessor, the software, and the data storage module are in telemetric or other communication with a computerized network, or with one or more other means for doing one or more of a) recording data obtained or contained in connection with the array, b) operating the array, and c) storing data contained or obtained in connection with operation of the array.

In one embodiment, a kit of a device of the invention may comprise a clamshell-type housing adapted and arranged to contain a plurality, such as inside 6, 8 or 10, electrodes, one or more preloaded gel packs adapted for facilitating all effective interface between the electrodes and the skin of the scalp, as well as electrodes, electrode holders, and a head frame. As another advantageous aspect of some preferred embodiments of the invention, the housing is provided with one or more means for operatively and reversibly containing one or more of the microprocessor, the data storage module and the software means such that substitute or interchangeable microprocessors, storage modules and software means in operative communication with the array can be exchanged, replaced or substituted when desired. Thus, one or more arrays of the invention can be put to a myriad of selected uses.

In one advantageous set of aspects, many different types of software can be used to direct or control the various functions, operational parameters, and characteristics of the invention, including the following, which are provided as examples, and not as limitations of the functions or uses of the invention. Thus, software for use with or in the invention may comprise one or more of software for setting the stimulation duration across all electrodes of the array; software for setting the stimulation intensity at each electrode; software for setting the stimulation polarity at each electrode; software for setting the stimulation DC offsets at each electrode; software for setting the time varying function at each electrode; software for setting the ramp up and ramp down times at each electrode; software for checking the impedance at each electrode; and software for monitoring the impedance at each electrode: software for controlling safety override voltages at each electrode; software for setting the lockout time period across all electrodes; software for effecting one or more electrode maintenance routines across all electrodes; software for checking one or more battery parameters before stimulation begins; software for locking the settings to prevent tampering with the software and certain settings of the device; software for operatively communicating with the array software interface for setting stimulation parameters; software for operatively connecting a plurality of arrays to one another, and software for performing finite element modeling.

Additional software includes one or more software for one or more of determining and redetermining the optimal spatial location of one or more electrodes with respect to the scalp and with respect to the housing, software for one or more of determining and redetermining the optimal polarity of each electrode at each location, software for one or more of determining and redetermining the intensity of the current delivery at each electrode location, software for one or more of determining and redetermining the time varying wave form with respect to each electrode; software for generating time varying functions that mimic one or more brain activities, software for detecting EEG signals, software for generating feedback to alter one or more electrical or structural brain activities, software for interpreting and classifying detected EEG activity as a desired or an undesirable brain state, and software for providing feedback to the subject in the form of one or more types of electrical brain stimulation, as well as software means for one or more of determining and redetermining one or more tasks of the arrays.

As yet another characteristic of certain embodiments of the invention, one or more of the microprocessor, the data storage module and the software can be reversibly provided in operation proximity to one or more electrodes of the array. Thus, arrays of the invention can be programmed and reprogrammed by switching out various physical and software components. In addition, one or more of the microprocessor, the data storage module and the software can be permanently provided in operation proximity to one or more electrodes of the array.

As yet other advantages of embodiments of the invention, the array of one or more of the housing and electrodes can be adapted and arranged for determining the respective optimal operational parameters and configurations of one or more external scalp electrodes, pluralities of electrodes or electrode arrays with respect to a single subject brain. Moreover, one or more of the microprocessor, the data storage module and the software can be adapted and arranged to be reconfigured during operation of the array on a subject. Thus, as arrays of the invention are operating and communicating with various systems, their various functions can be changed or redirected as wanted or needed.

As additional adaptive advantages and characteristics of some embodiments of the present invention, the present arrays can be provided in self-contained embodiments, or kits. Although many embodiments of self-contained arrays are within the spirit and scope of the invention, typical embodiments include those that are provided as kits. Thus, a typical kit embodiment of the present variably configurable electrode array would include at least one array, wherein the array comprises: at least two electrodes, wherein each of the electrodes is operationally connected to the other electrodes, or to at least one microprocessor; a housing adapted and arranged for variably positioning the electrodes with respect to one another, and for variably positioning each of the electrodes respectively in operational proximity to one or more regions, areas or points of a scalp of a subject upon which the array is placed; at least one microprocessor located in operational proximity to the housing, wherein the microprocessor is adapted and arranged to process data collected by means of the electrodes; and at least one data storage module located in operational proximity to the array, wherein the module is adapted and arranged to be operationally connectable to one or more of the at least two electrodes and the at least one microprocessor; and at least one software suitable for storing software, wherein the software is adapted and arranged for one or more of operating one or more functions of the array, storing data collected by the array and processing data. It may also include software necessary to operate the array in all desired aspects, and task software contained in operational connection or within the array housing directed toward one or more specific purposes.

A self-contained embodiment of the invention may also include wherein the task software is one or more from the group comprising language learning software, ability testing software, diagnostic software, and any other software adapted and arranged for effecting one or more diagnostic, evaluational teaching, and redirective tasks.

As yet another positive aspect, embodiments of the invention include also where pluralities of electrodes or pluralities of arrays are networked plurality of variably configurable electrode arrays as described herein, wherein the plurality of arrays are adapted and arranged to be in operative communication with one another while one or a plurality of the arrays are in operational proximity to one or a plurality of the scalps of one or more subjects. As in certain other embodiments of the present invention, networked pluralities of arrays of the invention can be adapted and arranged to measure, test, evaluate, teach, redirect, record and assess numerous abilities, characteristics, values, capabilities and aspects of one or more brains.

In accordance with the several objects of the invention, a variably configurable electrode array is provided in the context of effecting various methods, wherein one of the methods is a method for determining the optimum operational parameters of one or more neurological electrodes or electrode arrays, the method comprising the steps or actions of: recording one or more brain activities of a subject to obtain one or more brain electrical activity patterns of the subject brain during i) one or more desirable brain states, and ii) one or more undesirable brain states, to thereby obtain datasets with respect to each activity, wherein the datasets with respect to the desirable brain states and the undesirable brain states datasets are correlated; and then evaluating any of the correlated datasets or patterns obtained with respect to corresponding desirable and undesirable brain states to obtain one or more difference datasets; and then utilizing the difference datasets to effect a determination of one or more target regions, portions or locations of the subject brain. The present method may also comprise further the step or action of effecting stimulation of the determined target regions, portions or locations of the target brain with electrical NIBS to the extent necessary to effect desired changes in the brain patterns or activities.

As another advantage of the present method, one or more of the polarity, intensity, and spatial distribution of the effected stimulation can be utilized to produce a desired excitation or inhibition of one or more of the regions, portions or locations of the target brain. Moreover, the stimulation is adapted and arranged to effect the maximal desired influence at the one or more regions, portions or locations of the target brain such that changes in the brain effected by the NIBS influences the targets to move from one or more undesirable states to one or more desirable states.

In another significant aspect of many preferred embodiments of methods of the present technology, finite element modeling is used to filter or refine the datasets and images obtained by electrodes and arrays of the invention. As examples, finite element modeling of one or more of the target brain, scalp, skull and associated tissues is utilized in order to determine the most advantageous parameters of the various possible configurations and variations of the present electrodes and arrays.

Method of the present technology may also utilize wherein the brain activities are recorded by one or more of magnetoencephalography (MEG), electroencephalography (EEG), functional magnetic resonance imaging (fMRI), positron emission tomography (PET), single photon emission computed tomography (SPECT), electrocorticography (ECOG), structural magnetic resonance imaging (sMRI), diffusion tensor imaging (DTI), magnetic resonance spectroscopy (MRS), and/or functional near infrared spectroscopy (fNIRS) during desirable and non-desirable brain states, i.e. expert vs. novice, highly attentive vs. nonattentive, awake vs. fatigued, correct responses vs. incorrect responses, injured vs. uninjured.

In accordance with the many objects of the present invention, methods for determining the optimal operational parameters and configurations of one or more external scalp electrodes, pluralities of electrodes or electrode arrays with respect to a single subject brain, are provided. In one significant embodiment, the method comprises the steps or actions of: operating one or more of the electrodes or electrode arrays to create one or more recordings of activities, states, or structures of a subject brain to obtain data with respect to the one or more activities, states, or structures of the subject brain during one or more desirable brain states, and one or more undesirable brain states, to thereby collect obtained datasets regarding each activity, state or structure with respect to the desirable brain states and with respect to the undesirable brain states, wherein the obtained datasets are adaptable to one or more comparisons: then effecting one or a plurality of comparisons of the obtained datasets with respect to corresponding desirable and undesirable brain states to obtain one or more difference datasets; then evaluating the difference datasets to effect a determination of one or more target regions, portions or locations of the subject brain. The present method may also include the further step of utilizing the obtained datasets and the difference datasets to effect one or more redesigns or reconfigurations of the one or more external electrodes or electrode arrays to arrive at an improved or optimized electrode or electrode array.

As examples of the variability and adaptability of the present methods, electrodes and arrays, the one or more redesigns or reconfigurations can be made with respect to many factors, functions and uses. These include, as examples, one or more of the three-dimensional relationships between or among the electrodes, pluralities of electrodes or electrode arrays, the three-dimensional relationships between or among the electrodes, pluralities of electrodes or electrode arrays, one or more electrode carriers or frames, and the scalp upon which the electrodes, pluralities of electrodes or electrode arrays are placed.

This is also true with respect to those situations wherein the adaptations, redesigns or reconfigurations of the electrodes, pluralities of electrodes or electrode arrays are made with respect to one or more of the difference in images or patterns obtained, for example, as part of the present methods and arrays, finite element modeling in which the brain regions, portions, locations, or structures are selected in a brain virtualized in a finite element model can be used as a filter to determine the locations on the scalp where electrodes would be most effective in delivering current to the identified brain area. Examples of parameters that can be indicated by the finite element modeling include, as examples, the spatial location of electrodes on the scalp, the polarity of the electrode at each location, the intensity of the current delivery at each electrode location, and the time varying wave form at each electrode location.

The present method may also comprise the step or action of utilizing the improved or optimized electrode, plurality of electrodes or electrode array to stimulate the target brain to thereby test the design of the improved electrode or electrode array and to obtain additional datasets; as well as the step of utilizing the additional datasets to further redesign or reconfigure the improved electrode or plurality of electrodes in an array to arrive at a final electrode or plurality of electrodes in an array.

In accordance with yet additional positive aspects and adaptations of the present technology, one of the present methods includes that for determining the optimal operational parameters and configurations of one or more external scalp electrodes with respect to a plurality of subject brains, the method comprising the steps or actions of: creating one or more records of one or more brain activities, states, or structures with respect to the plurality of the subject brains to obtain data with respect to one or more brain electrical activities of the plurality of the subject brains during i) one or more desirable brain states, and ii) one or more undesirable brain states, to thereby collect obtained datasets regarding each activity, state, or structure with respect to the desirable brain states and with respect to the undesirable brain states, wherein the obtained datasets are adaptable to one or more comparisons; then effecting one or a plurality of comparisons of the obtained datasets with respect to corresponding desirable and undesirable brain states of the plurality of brains to obtain one or more difference datasets; and then evaluating the difference datasets to effect a determination of one or more target regions, portions or locations of the plurality of subject brains.

The ng-TDCS may accordingly be utilized for a number of different applications. One such application is training where ng-TDCS may be adapted and arranged to compare the performance of novices and experts to then target stimulation to facilitate the transition from novice to expert. The ng-TDCS stimulation could be applied to classroom learning in the full spectrum of topics, e.g., to learning new languages, learning to perform a complex motor task, to entrance exams including those for different schools and a full spectrum of other entrance exams. A portable TDCS unit could also make training in a variety of sports possible, e.g., swing training in golf, learning plays and defensive patterns in football, basketball, soccer, etc.

Another example of an application for ng-TDCS may be for various treatments where the ng-TDCS may be adapted and arranged to be used to image the brain when the behavior of the neurologically impaired individual was desirable and again in states where the behavior was undesirable. For example, when a person has high or low anxiety, when a person with schizophrenia is hallucinating or not, when a person with autism is making eye contact or not, when a person with post-traumatic stress disorder is having a nightmare or not, when a person with migraine headaches is in pain or not, when a person with chronic pain is having a painful experience or not, when a person with a phobia is in a fearful state or not, when a person with epilepsy is having a seizure or not, etc. Moreover, ng-TDCS could be used to aid in the transition from undesirable to desirable behavioral states.

Yet another example of an application for ng-TDCS may be for rehabilitation where the ng-TDCS stimulation could be used in the retraining of compensatory strategies, e.g., after a stroke, head injury, traumatic brain injury, brain surgery, etc.

Thus, in the same way, ng-TDCS compares novices and experts, neuroimaging could be performed on separate trials in the scanner(s) when performance is successful and when performance is unsuccessful. For example, in memory tasks the brain activity during incorrect responses could be subtracted from the activity during correct responses. This would show the brain regions that are critical for successful performance and these region(s) could be modeled with finite element modeling to generate electrode placements for ng-TDCS treatment that facilitate successful performance.

In addition, the effect of TDCS on the fractional anisotropy as measured with diffusion tensor imaging indicates that white matter tracts could be strengthened and perhaps even repaired in head injury and traumatic brain injury where breaks in the white matter connections between brain areas are thought to be important in the observed deficits.

Yet another application may include decision making where ng-TDCS can be adapted and arranged to be used to facilitate decision making strategies that are advantageous in specific tasks. Intuitive, deductive, and inductive reasoning could be imaged in the scanner(s) to delineate the brain structures critical to each type of decision making. Then these patterns of brain activation could be input into the finite element modeling routine to indicate the electrode positions that could be used to influence brain networks to engage preferentially in type of reasoning over others. Potential examples of this may include technical trading in the stock or commodities markets, shoot/no shoot training for law enforcement professionals, screening of baggage at airports, training to drive, detective work, military intelligence, surveillance, and reconnaissance operations, etc.

Yet another application may include enhanced response speed or accuracy where ng-TDCS can be adapted and arranged to bias the brain networks toward quick or careful responding to maximize speed or accuracy when one strategy benefits the task more than the other. This could be applied to technical trading in the commodities or stock markets, marksmanship, gaming, etc.

Yet another application may include reduction in distractions where ng-TDCS can similarly be adapted and arranged to aide in focus on a single line of information to rapidly induce a flow state. This would be beneficial in tasks where prolonged vigilance or focus is beneficial such as military intelligence, surveillance, and reconnaissance operations, gaming, or technical trading in the commodities or stock market, etc.

Yet another application may include treatment for natural declines and disorders of aging where ng-TDCS can be adapted and arranged to aide in reversing or slowing age related memory decline as well as memory decline in age related disorders such as dementia.

These particular applications for ng-TDCS are provided as examples and are not intended to be limiting. Other applications for ng-TDCS are, of course, intended to be included within the scope of this disclosure.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the light to physically incorporate into this specification any and all materials and information from any such cited patents or publications. The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth.

Under no circumstances may the patent be interpreted to be limited to the specific examples or embodiments or methods specifically disclosed herein. The terms and expressions that have been employed are used as terms of description and not of limitation, and there is no intent in the use of such terms and express ions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the Scope of this invention as defined by the appended claims.

The invention is described broadly and generically herein, while also providing descriptions Figures, photo-images and diagrams of various specific or exemplary embodiments of elements or portions of the invention. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A method of treating a subject, comprising:
   recording a first level brain activity of the subject corresponding to a low performance state;
   recording a second level brain activity of the subject corresponding to a high performance state;
   determining a difference between the recorded first level and the recorded second level to produce a difference image;
   modeling the difference image to determine a corresponding pattern of electrical activity;
   identifying one or more regions of maximal current density on a scalp surface corresponding to the pattern of electrical activity; and
   stimulating the one or more regions on the scalp surface such that the corresponding regions of the brain are stimulated.

2. The method of claim 1 wherein recording first level brain activity and second level brain activity comprises neuroimaging the brain of the subject.

3. The method of claim 2 wherein neuroimaging the brain comprises imaging via MEG, EEG, fMRI, PET, SPECT, ECOG, fNIRS, sMRI, DTI, or MRS.

4. The method of claim 1 wherein determining a difference comprises subtracting areas common to both the first level brain activity and second level brain activity such that the difference image comprises areas of brain activity that change between the low performance and high performance states.

5. The method of claim 1 wherein modeling the difference image comprises modeling via a finite element model to calculate the pattern of electrical activity.

6. The method of claim 1 wherein stimulating the one or more regions comprises non-invasively applying a stimulation to the scalp surface.

7. The method of claim 6 wherein the stimulation is selected from the group consisting of transcranial magnetic stimulation (TMS), repetitive TMS (rTMS), pulsed electromagnetic fields (PEMF), transcranial alternating current stimulation (TACS), transcranial random noise stimulation (TRNS), time varying electrical stimulation (TVES), and ultrasound brain stimulation (UBS).

8. The method of claim 1 wherein stimulating the one or more regions comprises applying a single electrode polarity to the scalp surface.

9. The method of claim 8 wherein applying a single electrode polarity comprises applying at least one anode to enhance brain activity or at least one cathode to suppress brain activity.

10. The method of claim 1 wherein stimulating the one or more regions comprises applying the stimulation over a ramp up period, a treatment period, and a ramp down period.

11. The method of claim 10 wherein the ramp up period ranges from 10 secs to 15 mins.

12. The method of claim 10 wherein the ramp up period is variable.

13. The method of claim 10 wherein the ramp down period is variable.

14. The method of claim 10 wherein the treatment period ranges from 0.1 mins to 60 mins.

15. The method of claim 10 wherein the treatment period comprises applying time-varying stimulation having a frequency of 0 to 10,000 Hz.

16. The method of claim 10 wherein the treatment period has a current which ranges from 0.1 mA to 4 mA.

17. The method of claim 10 wherein the ramp down period ranges from 10 secs to 15 mins.

18. The method of claim 1 wherein stimulating comprises positioning at least one electrode upon the scalp surface.

19. The method of claim 18 wherein positioning at least one electrode comprises securing the at least one electrode to a head of the subject.

20. The method of claim 19 further comprising introducing a conductive medium within a cavity or channel between the at least one electrode and the scalp surface.

21. The method of claim 1 wherein stimulating the one or more regions comprises reconfiguring an electrode assembly in two or more electrode components for positioning relative to the corresponding regions of the brain.

22. The method of claim 21 wherein positioning the two or more electrode components comprises supporting the components via a head frame configured to individually position the components relative to the regions of the brain.

23. The method of claim 1 wherein stimulating the one or more regions comprises driving a plurality of channels where each channel provides a current source independent from one another.

24. The method of claim 23 further comprising monitoring for an open circuit in each of the plurality of channels.

25. The method of claim 23 further comprising monitoring an impedance over the plurality of channels to determine a mean impedance value.

26. The method of claim 25 further comprising adjusting the current source over an electrode-to-scalp connection impedance range of 4 to 40,000 Ohms.

27. The method of claim 1 further comprising locking out for a predetermined period of time any further stimulation once a treatment session has been completed.

28. An apparatus comprising:
   at least one processor; and
   a non-transitory computer-readable medium having stored thereon instructions to cause the at least one processor to execute a method, the method comprising:
      recording a first level brain activity of the subject corresponding to a low performance state;
      recording a second level brain activity of the subject corresponding to a high performance state;
      determining a difference between the recorded first level and the recorded second level to produce a difference image;
      modeling the difference image to determine a corresponding pattern of electrical activity;
      identifying one or more regions of maximal current density on a scalp surface corresponding to the pattern of electrical activity; and
      causing at least one electrode to stimulate the one or more regions on the scalp surface such that the corresponding regions of the brain are stimulated.

29. A non-transitory computer readable medium having stored thereon instructions to cause at least one processor to execute a method, the method comprising:
   recording a first level brain activity of the subject corresponding to a low performance state;
   recording a second level brain activity of the subject corresponding to a high performance state;
   determining a difference between the recorded first level and the recorded second level to produce a difference image;
   modeling the difference image to determine a corresponding pattern of electrical activity;

identifying one or more regions of maximal current density on a scalp surface corresponding to the pattern of electrical activity; and causing at least one electrode to stimulate the one or more regions on the scalp surface such that the corresponding regions of the brain are stimulated.

* * * * *